US010577356B2

(12) United States Patent
Reggio et al.

(10) Patent No.: US 10,577,356 B2
(45) Date of Patent: *Mar. 3, 2020

(54) BETA-ARRESTIN-BIASED CANNABINOID $CB_1$ RECEPTOR AGONISTS AND METHODS FOR MAKING AND USING THEM

(71) Applicant: The University of North Carolina at Greensboro, Greensboro, NC (US)

(72) Inventors: Patricia H. Reggio, Greensboro, NC (US); Derek M. Shore, Pine Hall, NC (US); Dow P. Hurst, Greensboro, NC (US)

(73) Assignee: The University of North Carolina at Greensboro, Greensboro, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/153,180

(22) Filed: Oct. 5, 2018

(65) Prior Publication Data

US 2019/0040045 A1    Feb. 7, 2019

Related U.S. Application Data

(63) Continuation of application No. 15/383,922, filed on Dec. 19, 2016, now Pat. No. 10,118,914, which is a continuation of application No. PCT/US2015/035653, filed on Jun. 12, 2015.

(60) Provisional application No. 62/015,289, filed on Jun. 20, 2014.

(51) Int. Cl.
| | |
|---|---|
| *C07D 405/12* | (2006.01) |
| *C07D 405/14* | (2006.01) |
| *C07D 471/04* | (2006.01) |
| *C07D 401/12* | (2006.01) |
| *C07D 209/42* | (2006.01) |

(52) U.S. Cl.
CPC ........ *C07D 405/12* (2013.01); *C07D 209/42* (2013.01); *C07D 401/12* (2013.01); *C07D 405/14* (2013.01); *C07D 471/04* (2013.01)

(58) Field of Classification Search
None
See application file for complete search history.

(56) References Cited

U.S. PATENT DOCUMENTS

| | | | |
|---|---|---|---|
| 2009/0047246 A1 | 2/2009 | Beigelman et al. | |
| 2009/0253682 A1 | 10/2009 | Termin et al. | |
| 2010/0292204 A1 | 11/2010 | Lange et al. | |
| 2016/0194284 A1* | 7/2016 | Thakur | C07D 213/74 514/235.5 |

FOREIGN PATENT DOCUMENTS

| | | |
|---|---|---|
| WO | 2012/117216 A1 | 9/2012 |
| WO | 2015/195486 A1 | 12/2015 |

OTHER PUBLICATIONS

Mahmoud et al., Structure-Activity Relationship Study of Indole-2-carboxamides Identified a Potent Allosteric Modulator for the Cannabinoid Receptor (CB1). Journal of Medicinal Chemistry, 2013, 56, 7965-7975.*
Pinar-Sueiro et al., Cannabinoid application is glaucoma. Archivos De La Sociedad Espanola De Oftalmologia, 2011, 86, 16-23.*
Coleman et al., The other randomization—methods for labeling drug kits. Contemporary Clinical Trials, 2014, 38, 270-274.*
Iliff et al. "Parameterization of Org27569: an allosteric modulator of the cannabinoid CB1 G protein-coupled receptor." J Comput Chem. Apr. 27, 2011; 32(10): 2119-2126.
Piscitelli et al. "Indole-2-carboxamides as Allosteric Modulators of the Cannibinoid $CB_1$ Receptor." *J.Med. Chem.* May 9, 2012; 55 (11): 5627-5631.
PCT/US2015/035653, "International Search Report and Written Opinion", dated Nov. 24, 2015, 13 pages.
Shore, et al. "Rational design of neutral allosteric modulators of the $CB_1$ receptor with improved receptor interactions and unique pharmacology." 23$^{rd}$ Annual Symposium of the International Cannabinoid Research Society. Presented Jun. 21, 2013, Vancouver, British Columbia, Canada.

* cited by examiner

*Primary Examiner* — Po-Chih Chen
(74) *Attorney, Agent, or Firm* — Kilpatrick Townsend & Stockton LLP

(57) ABSTRACT

The present invention provides compounds having a $CB_1$ receptor-binding moiety and a directing moiety. In related aspects, the invention provides pharmaceutical compositions containing compounds of the invention, methods for inhibiting a pathway modulated in part by the $CB_1$ receptor activity, and methods for treating a condition or disorder mediated in part by $CB_1$ receptor activity. In certain embodiments, the compounds are compounds of Formula I. Methods of preparing compounds of Formula I are also described. In another aspect, the invention provides methods of identifying a selective agonist of the beta-arrestin pathway over the G-protein pathway.

11 Claims, 6 Drawing Sheets

ORG27569

Compound 1

Compound 2

Compound 3

Compound 4

| Allosteric Modulator | Experimental | |
|---|---|---|
| | CP55,940's $B_{max}$ % equilibrium binding (10 μM of allosteric modulator) | CP55,940's Efficacy [$^{35}$S]GTPγS binding (% inhibition, 1 μM of modulator) |
| ORG27569 | 212 | 100 |
| Compound 1 | 182 | 57 |
| Compound 2 | 237 | 100 |
| Compound 4 | 100 | 100 |
| Compound 3 | 75 | 0 |

BETA-ARRESTIN-BIASED CANNABINOID CB₁ RECEPTOR AGONISTS AND METHODS FOR MAKING AND USING THEM

CROSS-REFERENCE TO RELATED APPLICATIONS

This application is a continuation of U.S. patent application Ser. No. 15/383,922, filed Dec. 19, 2016, which is a continuation of Intl. Pat. Appl. No. PCT/US2015/035653, filed Jun. 12, 2015, which claims priority to U.S. Provisional Pat. Appl. No. 62/015,289, filed Jun. 20, 2014, which applications are incorporated herein by reference in their entirety.

STATEMENT AS TO RIGHTS TO INVENTIONS MADE UNDER FEDERALLY SPONSORED RESEARCH AND DEVELOPMENT

This work was supported by the NIH National Institute on Drug Abuse under Grant Nos. RO1 DA003924 and KO5 DA021358. The government has certain rights in the invention.

BACKGROUND OF THE INVENTION

Cannabinoid agonists have been shown to lower intraocular pressure in glaucoma; produce pain relief; lessen nausea associated with chemotherapy; produce a neuroprotective effect in neurodegenerative diseases such as Alzheimer's disease and amyotrophic lateral sclerosis (ALS); and act as appetite stimulants. Commercial development of ligands that bind to the cannabinoid $CB_1$ receptor have hit major roadblocks due to psychoactive effects associated with agonists and depressive effects, including suicidal ideation, associated with inverse agonists. Until very recently, the focus of cannabinoid compound design was on the G-protein signaling pathway. It has now become clear that there are two signaling pathways for the $CB_1$ receptor, the long-appreciated $G_{i/o}$ pathway (which leads to a pERK signal that can be abrogated with pertussis toxin, a $G_{i/o}$ toxin) and a beta-arrestin mediated pathway that leads to production of pERK that is insensitive to pertussis toxin. Ligands that favor such a second pathway have been discovered in other receptor fields (the beta-2-adrenergic and delta-opioid fields), but these latter ligands actually signal through both pathways, simply favoring the beta-arrestin mediated pathway. What is needed are tools for determining which effects of $CB_1$ modulators arise from which pathways and therapeutically effective cannabinoid $CB_1$ receptor ligands having reduced adverse side effects. The present invention meets these and other needs.

BRIEF SUMMARY OF THE INVENTION

In one aspect, the invention provides a compound having a $CB_1$ receptor-binding moiety and a directing moiety, wherein the $CB_1$ receptor-binding moiety interacts in a non-covalent manner with one or more amino acid residues selected from the group consisting of A6.53(361), I6.54 (362), Y6.57(365), D6.58(366), K(370), M(371), N(372), K(373), L(374), I(375), K(376), and F7.35(379) of the $CB_1$ receptor, and wherein the directing moiety prevents binding of the compound to one more amino acid residues selected from the group consisting of P6.50(358), A6.53(361), I6.54 (362), Y6.57(365), M(371), F7.35(379), C7.38(382), and S7.39(383) of the $CB_1$ receptor.

In certain embodiments, the compound has the Formula I:

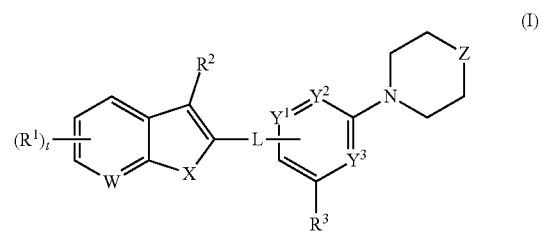

or a pharmaceutically acceptable salt thereof; wherein
$R^1$ is selected from the group consisting of halo, cyano, nitro, and acetyl;
$R^2$ is selected from the group consisting of $C_{1-12}$ alkyl, $C_{0-4}$ alkyl-$C_{3-8}$ cycloalkyl, and $C_{0-4}$ alkyl-$C_{6-10}$ aryl,
$R^3$ is selected from the group consisting of H, $C_3$-$C_{12}$ alkyl, $C_3$-$C_8$ cycloalkyl, 4- to 8-membered heterocyclyl, $C_6$-$C_{10}$ aryl, and 5- to 10-membered heteroaryl;
W is selected from the group consisting of N and $CR^{1a}$, wherein $R^{1a}$ is selected from the group consisting of H and $R^1$;
X is selected from the group consisting of O, C=O, and $NR^4$, wherein $R^4$ is selected from the group consisting of H and $C_{1-6}$ alkyl;
$Y^1$, $Y^2$, and $Y^3$ are independently selected from the group consisting of N and CH;
Z is selected from the group consisting of O, $CH_2$, and $NR^4$, wherein $R^4$ is selected from the group consisting of H and $C_{1-6}$ alkyl;
subscript t is 0 when W is $CR^{1a}$ and $R^{1a}$ is $R^1$;
subscript t is 1 when W is N or when W is $CR^{1a}$ and $R^{1a}$ is H; and
L is selected from the group consisting of

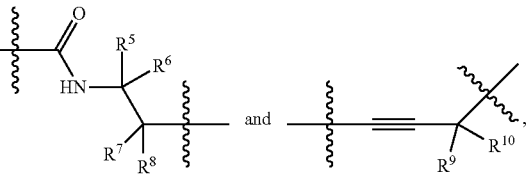

wherein
$R^5$, $R^6$, $R^7$, and $R^8$ are independently selected from the group consisting of H and OH, provided that at least one of $R^5$ and $R^6$ is H and at least one of $R^7$ and $R^8$ is H, or
one of $R^5$ and $R^6$ is taken together with one of $R^7$ and $R^8$ to form a 5- to 6-membered saturated carbocyclic or heterocyclic group, or
$R^5$ and $R^7$ are absent and $R^6$ and $R^8$ are taken together to form a 5- to 6-membered unsaturated carbocyclic or heterocyclic group, and
$R^9$ and $R^{10}$ are independently selected from the group consisting of H and OH, provided that at least of $R^9$ and $R^{10}$ is H, and;
provided that if $R^2$ is $C_{1-12}$ alkyl, $R^5$, $R^6$, $R^7$, and $R^8$ are H, and $Y^1$, $Y^2$, and $Y^3$ are CH, then $R^3$ is selected from the group consisting of $C_3$-$C_{12}$ alkyl, $C_3$-$C_8$ cycloalkyl, 4- to 8-membered heterocyclyl, $C_6$-$C_{10}$ aryl, and 5- to 10-membered heteroaryl.

In a related aspect, the invention provides methods for preparing compounds of Formula I.

In another aspect, the invention provides pharmaceutical compositions containing a compound of the invention and one or more pharmaceutically acceptable excipients. In a related aspect, the invention provides a kit having a composition of the invention and instructions for use.

In another aspect, the invention provides methods of inhibiting a pathway modulated in part by $CB_1$ receptor activity. The methods include the step of contacting a cell with a compound of the invention.

In another aspect, the invention provides methods of treating a condition or disorder mediated in part by $CB_1$ receptor activity in a patient in need thereof. The methods include administering to the patient an effective amount of a compound of the invention.

In another aspect, the invention provides methods of identifying a selective agonist of the beta-arrestin pathway over the G-protein pathway. The methods include identifying a compound that binds in a non-covalent manner with one or more $CB_1$ receptor amino acid residues selected from the group consisting of A6.53(361), I6.54(362), Y6.57(365), D6.58(366), K(370), M(371), N(372), K(373), L(374), I(375), K(376), and F7.35(379); and determining that the compound does not bind to one more $CB_1$ receptor amino acid residues selected from the group consisting of P6.50(358), A6.53(361), I6.54(362), Y6.57(365), M(371), F7.35(379), C7.38(382), and S7.39(383).

DETAILED DESCRIPTION OF THE INVENTION

I. General

Figure 1:
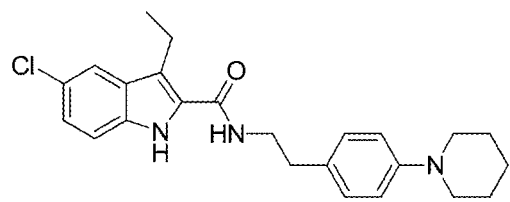
FIG. 1 shows ORG27569 and compounds of the invention (Compound 1; Compound 2; Compound 3).
Figure 1:
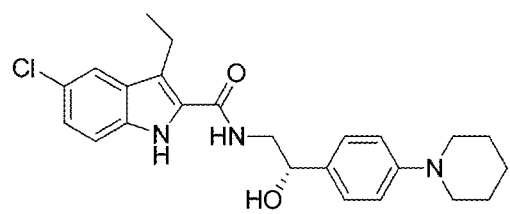
Figure 1:
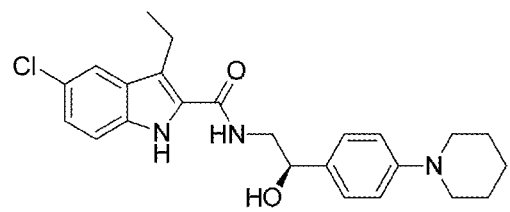
Figure 1:
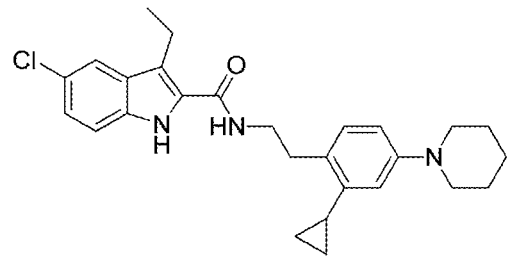
Figure 1:
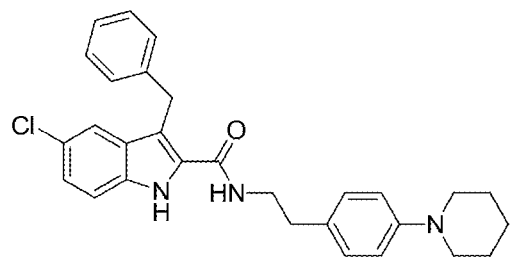

The present invention is based on the surprising discovery of cannabinoid $CB_1$ receptor ligands that produce no effect on the $G_{i/o}$ pathway, but signal completely via beta-arrestin. The appeal of such biased cannabinoid $CB_1$ ligands is that for the first time, the plethora of effects caused by $CB_1$ agonists can be sorted between the two pathways.

II. Definitions

As used herein, the terms "cannabinoid $CB_1$ receptor" and "$CB_1$ receptor" refer to the Class A G-protein coupled receptor (GPCR) found primarily at central and peripheral nerve terminals. The human $CB_1$ receptor, as a non-limiting example, is entered into the UniProtKB/Swiss-Prot database under accession number P21544.

As used herein, the term "$CB_1$ receptor orthosteric site" refers to the site of binding of the majority of endogenous and synthetic ligands, such as anandamide, $\Delta^9$-THC, and CP55,940, to the $CB_1$ receptor. The orthosteric site is commonly understood to be topographically defined by amino acid residues including, but not limited to, F2.57(170), K3.28(192), V3.32(196), F3.36(200), W4.64(255), Y5.39 (275), F5.42(278), W5.43(279), W6.48(356), M7.40(384), and L7.43(387).

As used herein, the term "$CB_1$ receptor allosteric site" refers to the site of binding of endogenous and synthetic ligands, which is topographically distinct from the $CB_1$ receptor orthosteric site. Ligand binding at the allosteric site can promote or inhibit binding of ligands at the orthosteric site. Amino acid residues defining the $CB_1$ receptor allosteric site include, but are not limited to, K3.28(192), F3.36 (200), W5.43(279), W6.48(356), D6.58(366), and F3.25 (192).

As used herein, the term "$CB_1$ receptor-binding moiety" refers to a molecule or a portion of a molecule that non-covalently interacts with a region of the $CB_1$ receptor. In certain embodiments, the $CB_1$ receptor-binding moiety binds to the $CB_1$ receptor allosteric site. In certain embodiments, the $CB_1$ receptor binding moiety binds the $CB_1$ receptor between transmembrane helix (TMH) 6 and TMH7. In certain embodiments, the $CB_1$ receptor binding moiety binds extracellular loop 3 of the $CB_1$ receptor.

As used herein, the term "directing moiety" refers to a portion of a molecule that prevents binding of the molecule to one or more residues selected from the group consisting of P6.50(358), A6.53(361), I6.54(362), Y6.57(365), M(371), F7.35(379), C7.38(382), and S7.39(383).

As used herein, the term "non-covalent interaction" refers to electromagnetic interaction between two or more molecules (or two or more portions of one or more molecules) by electrostatic interaction, hydrogen bonding, π-π interactions, hydrophobic interactions (van der Waals forces), or a combination thereof.

As used herein, the term "alkyl" refers to a straight or branched, saturated, aliphatic radical having the number of carbon atoms indicated. Alkyl can include any number of carbons, such as $C_{1-2}$, $C_{1-3}$, $C_{1-4}$, $C_{1-5}$, $C_{1-6}$, $C_{1-7}$, $C_{1-8}$, $C_{1-9}$, $C_{1-10}$, $C_{2-3}$, $C_{2-4}$, $C_{2-5}$, $C_{2-6}$, $C_{3-4}$, $C_{3-5}$, $C_{3-6}$, $C_{4-5}$, $C_{4-6}$ and $C_{5-6}$. For example, $C_{1-6}$ alkyl includes, but is not limited to, methyl, ethyl, propyl, isopropyl, butyl, isobutyl, sec-butyl, tert-butyl, pentyl, isopentyl, hexyl, etc. Alkyl can also refer to alkyl groups having up to 20 carbons atoms, such as, but not limited to heptyl, octyl, nonyl, decyl, etc. Alkyl groups can be substituted or unsubstituted. "Substituted alkyl" groups can be substituted with one or more groups selected from halo, hydroxy, amino, alkylamino, amido, acyl, nitro, cyano, and alkoxy.

As used herein, the term "cycloalkyl" refers to a saturated or partially unsaturated, monocyclic, fused bicyclic or bridged polycyclic ring assembly containing from 3 to 12 ring atoms, or the number of atoms indicated. Cycloalkyl can include any number of carbons, such as $C_{3-6}$, $C_{4-6}$, $C_{5-6}$, $C_{3-8}$, $C_{4-8}$, $C_{5-8}$, $C_{6-8}$, $C_{3-9}$, $C_{3-10}$, $C_{3-11}$, and $C_{3-12}$. Saturated monocyclic cycloalkyl rings include, for example, cyclopropyl, cyclobutyl, cyclopentyl, cyclohexyl, and cyclooctyl. Saturated bicyclic and polycyclic cycloalkyl rings include, for example, norbornane, [2.2.2] bicyclooctane, decahydronaphthalene and adamantane. Cycloalkyl groups can also be partially unsaturated, having one or more double or triple bonds in the ring. Representative cycloalkyl groups that are partially unsaturated include, but are not limited to, cyclobutene, cyclopentene, cyclohexene, cyclohexadiene (1,3- and 1,4-isomers), cycloheptene, cycloheptadiene, cyclooctene, cyclooctadiene (1,3-, 1,4- and 1,5-isomers), norbornene, and norbornadiene. When cycloalkyl is a saturated monocyclic $C_{3-8}$ cycloalkyl, exemplary groups include, but are not limited to cyclopropyl, cyclobutyl, cyclopentyl, cyclohexyl, cycloheptyl and cyclooctyl. When cycloalkyl is a saturated monocyclic $C_{3-6}$ cycloalkyl, exemplary groups include, but are not limited to cyclopropyl, cyclobutyl, cyclopentyl, and cyclohexyl. Cycloalkyl groups can be substituted or unsubstituted. "Substituted cycloalkyl" groups can be substituted with one or more groups selected from halo, hydroxy, amino, alkylamino, amido, acyl, nitro, cyano, and alkoxy.

As used herein, the term "aryl" refers to an aromatic ring system having any suitable number of ring atoms and any suitable number of rings. Aryl groups can include any suitable number of ring atoms, such as 6, 7, 8, 9, 10, 11, 12, 13, 14, 15 or 16 ring atoms, as well as from 6 to 10, 6 to 12, or 6 to 14 ring members. Aryl groups can be monocyclic, fused to form bicyclic or tricyclic groups, or linked by a bond to form a biaryl group. Representative aryl groups include phenyl, naphthyl and biphenyl. Other aryl groups include benzyl, having a methylene linking group. Some aryl groups have from 6 to 12 ring members, such as phenyl, naphthyl or biphenyl. Other aryl groups have from 6 to 10 ring members, such as phenyl or naphthyl. Some other aryl groups have 6 ring members, such as phenyl. Aryl groups can be substituted or unsubstituted. "Substituted aryl" groups can be substituted with one or more groups selected from halo, hydroxy, amino, alkylamino, amido, acyl, nitro, cyano, and alkoxy.

As used herein, the term "heterocyclyl" refers to refers to a saturated ring system having from 3 to 12 ring members and from 1 to 4 heteroatoms of N, O and S. Additional heteroatoms can also be useful, including, but not limited to, B, Al, Si and P. The heteroatoms can also be oxidized, such as, but not limited to, —S(O)— and —S(O)$_2$—. Heterocyclyl groups can include any number of ring atoms, such as, 3 to 6, 4 to 6, 5 to 6, 3 to 8, 4 to 8, 5 to 8, 6 to 8, 3 to 9, 3 to 10, 3 to 11, or 3 to 12 ring members. Any suitable number of heteroatoms can be included in the heterocyclyl groups, such as 1, 2, 3, or 4, or 1 to 2, 1 to 3, 1 to 4, 2 to 3, 2 to 4, or 3 to 4. The heterocyclyl group can include groups such as aziridine, azetidine, pyrrolidine, piperidine, azepane, azocane, quinuclidine, pyrazolidine, imidazolidine, piperazine (1,2-, 1,3- and 1,4-isomers), oxirane, oxetane, tetrahydrofuran, oxane (tetrahydropyran), oxepane, thiirane, thietane, thiolane (tetrahydrothiophene), thiane (tetrahydrothiopyran), oxazolidine, isoxazolidine, thiazolidine, isothiazolidine, dioxolane, dithiolane, morpholine, thiomorpholine, dioxane, or dithiane. The heterocyclyl groups can also be fused to aromatic or non-aromatic ring systems to form members including, but not limited to, indoline. Heterocyclyl groups can be unsubstituted or substituted. "Substituted heterocyclyl" groups can be substituted with one or more groups selected from halo, hydroxy, amino, oxo (=O), alkylamino, amido, acyl, nitro, cyano, and alkoxy.

The heterocyclyl groups can be linked via any position on the ring. For example, aziridine can be 1- or 2-aziridine, azetidine can be 1- or 2-azetidine, pyrrolidine can be 1-, 2- or 3-pyrrolidine, piperidine can be 1-, 2-, 3- or 4-piperidine, pyrazolidine can be 1-, 2-, 3-, or 4-pyrazolidine, imidazolidine can be 1-, 2-, 3- or 4-imidazolidine, piperazine can be 1-, 2-, 3- or 4-piperazine, tetrahydrofuran can be 1- or 2-tetrahydrofuran, oxazolidine can be 2-, 3-, 4- or 5-oxazolidine, isoxazolidine can be 2-, 3-, 4- or 5-isoxazolidine, thiazolidine can be 2-, 3-, 4- or 5-thiazolidine, isothiazolidine can be 2-, 3-, 4- or 5-isothiazolidine, and morpholine can be 2-, 3- or 4-morpholine.

When heterocyclyl includes 3 to 8 ring members and 1 to 3 heteroatoms, representative members include, but are not limited to, pyrrolidine, piperidine, tetrahydrofuran, oxane, tetrahydrothiophene, thiane, pyrazolidine, imidazolidine, piperazine, oxazolidine, isoxazolidine, thiazolidine, isothiazolidine, morpholine, thiomorpholine, dioxane and dithiane. Heterocyclyl can also form a ring having 5 to 6 ring members and 1 to 2 heteroatoms, with representative members including, but not limited to, pyrrolidine, piperidine, tetrahydrofuran, tetrahydrothiophene, pyrazolidine, imidazolidine, piperazine, oxazolidine, isoxazolidine, thiazolidine, isothiazolidine, and morpholine.

As used herein, the term "heteroaryl" refers to a monocyclic or fused bicyclic or tricyclic aromatic ring assembly containing 5 to 16 ring atoms, where from 1 to 5 of the ring atoms are a heteroatom such as N, O or S. Additional heteroatoms can also be useful, including, but not limited to, B, Al, Si and P. The heteroatoms can also be oxidized, such as, but not limited to, —S(O)— and —S(O)$_2$—. Heteroaryl groups can include any number of ring atoms, such as 3 to 6, 4 to 6, 5 to 6, 3 to 8, 4 to 8, 5 to 8, 6 to 8, 3 to 9, 3 to 10, 3 to 11, or 3 to 12 ring members. Any suitable number of heteroatoms can be included in the heteroaryl groups, such as 1, 2, 3, 4, or 5, or 1 to 2, 1 to 3, 1 to 4, 1 to 5, 2 to 3, 2 to 4, 2 to 5, 3 to 4, or 3 to 5. Heteroaryl groups can have from 5 to 8 ring members and from 1 to 4 heteroatoms, or from 5 to 8 ring members and from 1 to 3 heteroatoms, or from 5 to 6 ring members and from 1 to 4 heteroatoms, or from 5 to 6 ring members and from 1 to 3 heteroatoms. The heteroaryl group can include groups such as pyrrole, pyridine, imidazole, pyrazole, triazole, tetrazole, pyrazine, pyrimidine, pyridazine, triazine (1,2,3-, 1,2,4- and 1,3,5-isomers), thiophene, furan, thiazole, isothiazole, oxazole, and isoxazole. The heteroaryl groups can also be fused to aromatic ring systems, such as a phenyl ring, to form members including, but not limited to, benzopyrroles such as indole and isoindole, benzopyridines such as quinoline and isoquinoline, benzopyrazine (quinoxaline), benzopyrimidine (quinazoline), benzopyridazines such as phthalazine and cinnoline, benzothiophene, and benzofuran. Other heteroaryl groups include heteroaryl rings linked by a bond, such as bipyridine. Heteroaryl groups can be substituted or unsubstituted. "Substituted heteroaryl" groups can be substituted with one or more groups selected from halo, hydroxy, amino, alkylamino, amido, acyl, nitro, cyano, and alkoxy.

The heteroaryl groups can be linked via any position on the ring. For example, pyrrole includes 1-, 2- and 3-pyrrole, pyridine includes 2-, 3- and 4-pyridine, imidazole includes 1-, 2-, 4- and 5-imidazole, pyrazole includes 1-, 3-, 4- and 5-pyrazole, triazole includes 1-, 4- and 5-triazole, tetrazole includes 1- and 5-tetrazole, pyrimidine includes 2-, 4-, 5- and 6-pyrimidine, pyridazine includes 3- and 4-pyridazine, 1,2,3-triazine includes 4- and 5-triazine, 1,2,4-triazine includes 3-, 5- and 6-triazine, 1,3,5-triazine includes 2-triazine, thiophene includes 2- and 3-thiophene, furan includes 2- and 3-furan, thiazole includes 2-, 4- and 5-thiazole, isothiazole includes 3-, 4- and 5-isothiazole, oxazole includes 2-, 4- and 5-oxazole, isoxazole includes 3-, 4- and 5-isoxazole, indole includes 1-, 2- and 3-indole, isoindole includes 1- and 2-isoindole, quinoline includes 2-, 3- and 4-quinoline, isoquinoline includes 1-, 3- and 4-isoquinoline, quinazoline includes 2- and 4-quinazoline, cinnoline includes 3- and 4-cinnoline, benzothiophene includes 2- and 3-benzothiophene, and benzofuran includes 2- and 3-benzofuran.

Some heteroaryl groups include those having from 5 to 10 ring members and from 1 to 3 ring atoms including N, O or S, such as pyrrole, pyridine, imidazole, pyrazole, triazole, pyrazine, pyrimidine, pyridazine, triazine (1,2,3-, 1,2,4- and 1,3,5-isomers), thiophene, furan, thiazole, isothiazole, oxazole, isoxazole, indole, isoindole, quinoline, isoquinoline, quinoxaline, quinazoline, phthalazine, cinnoline, benzothiophene, and benzofuran. Other heteroaryl groups include those having from 5 to 8 ring members and from 1 to 3 heteroatoms, such as pyrrole, pyridine, imidazole, pyrazole, triazole, pyrazine, pyrimidine, pyridazine, triazine (1,2,3-, 1,2,4- and 1,3,5-isomers), thiophene, furan, thiazole, isothiazole, oxazole, and isoxazole. Some other heteroaryl groups include those having from 9 to 12 ring members and from 1 to 3 heteroatoms, such as indole, isoindole, quinoline, isoquinoline, quinoxaline, quinazoline, phthalazine, cinnoline, benzothiophene, benzofuran and bipyridine. Still other heteroaryl groups include those having from 5 to 6 ring members and from 1 to 2 ring atoms including N, O or S, such as pyrrole, pyridine, imidazole, pyrazole, pyrazine, pyrimidine, pyridazine, thiophene, furan, thiazole, isothiazole, oxazole, and isoxazole.

Some heteroaryl groups include from 5 to 10 ring members and only nitrogen heteroatoms, such as pyrrole, pyridine, imidazole, pyrazole, triazole, pyrazine, pyrimidine, pyridazine, triazine (1,2,3-, 1,2,4- and 1,3,5-isomers), indole, isoindole, quinoline, isoquinoline, quinoxaline, quinazoline, phthalazine, and cinnoline. Other heteroaryl groups include from 5 to 10 ring members and only oxygen heteroatoms, such as furan and benzofuran. Some other heteroaryl groups include from 5 to 10 ring members and only sulfur heteroatoms, such as thiophene and benzothiophene. Still other heteroaryl groups include from 5 to 10 ring members and at least two heteroatoms, such as imidazole, pyrazole, triazole, pyrazine, pyrimidine, pyridazine, triazine (1,2,3-, 1,2,4- and 1,3,5-isomers), thiazole, isothiazole, oxazole, isoxazole, quinoxaline, quinazoline, phthalazine, and cinnoline.

As used herein, the terms "halo" and "halogen" refer to fluorine, chlorine, bromine, iodine, and monovalent radicals thereof.

As used herein, the term "acyl," by itself or as part of another substituent, refers to a radical containing an alkyl group, as defined herein, bound to the carbon atom of a carbonyl group, the carbonyl carbon atom further being the point of attachment of the radical.

As used herein, the term "amino," by itself or as a part of another substituent, refers to a radical containing a nitrogen atom bound to two or three atoms selected from hydrogen and carbon, the nitrogen atom further being the point of attachment of the radical.

As used herein, the term "amido," by itself or as part of another substituent, refers to a radical containing an acyl group, as defined herein, bound to the nitrogen atom of an amino group, the carbonyl carbon atom or the nitrogen atom further being the point of attachment of the radical.

As used herein, the term "composition" encompasses a product containing the specified ingredients in the specified amounts, as well as any product, which results, directly or indirectly, from combination of the specified ingredients in the specified amounts. By "pharmaceutically acceptable" it is meant that a component of a composition such as a carrier, diluent, or excipient is compatible with the other ingredients of the formulation and not deleterious to the recipient thereof.

As used herein, the "term pharmaceutically acceptable excipient" refers to a substance that aids the administration of an active agent to and absorption by a subject. Pharmaceutical excipients useful in the present invention include, but are not limited to, binders, fillers, disintegrants, lubricants, coatings, sweeteners, flavors and colors. One of skill in the art will recognize that other pharmaceutical excipients are useful in the present invention.

As used herein, the term "treating" refers to any indicia of success in the treatment or amelioration of an injury, pathology, condition, or symptom (e.g., pain), including any objective or subjective parameter such as abatement; remission; diminishing of symptoms or making the symptom, injury, pathology or condition more tolerable to the patient; decreasing the frequency or duration of the symptom or condition; or, in some situations, preventing the onset of the symptom or condition. The treatment or amelioration of symptoms can be based on any objective or subjective parameter including, e.g., the result of a physical examination.

As used herein, the term "administering" refers to oral, topical, parenteral, intravenous, intraperitoneal, intramuscular, intralesional, intranasal, subcutaneous, or intrathecal administration to a subject, as well administration as a suppository or the implantation of a slow-release device, e.g., a mini-osmotic pump, in the subject.

As used herein, the "term effective amount" refers to a dose that produces a therapeutic effect for which it is administered. The exact dose will depend on the purpose of the treatment, and will be ascertainable by one skilled in the art using known techniques (see, e.g., Lieberman, *Pharmaceutical Dosage Forms* (vols. 1-3, 1992); Lloyd, *The Art, Science and Technology of Pharmaceutical Compounding* (1999); Pickar, *Dosage Calculations* (1999); and *Remington: The Science and Practice of Pharmacy*, 20th Edition, 2003, Gennaro, Ed., Lippincott, Williams & Wilkins).

As used herein, the term "beta-arrestin pathway" refers to a signaling cascade characterized by one or more steps including, but not limited to, binding of beta-arrestin to nonreceptor tyrosine kinase c-Src and activation of ERK1/2 phosphorylation via the β2-adrenergic receptor.

As used herein, the term "G-protein pathway" refers to a signaling cascade characterized by one or more steps including, but not limited to, activation of the pertussis toxin (PTX)-sensitive inhibitory G ($G_{i/o}$) protein, stimulation of adenylyl cyclase via $G_s$, and phosphorylation and activation of mitogen-activated protein kinases (MAPKs).

III. Compounds

In a first aspect, the invention provides a compound having: a) a $CB_1$ receptor-binding moiety, and b) a directing moiety. The $CB_1$ receptor-binding moiety interacts in a non-covalent manner with one or more amino acid residues selected from the group consisting of A6.53(361), I6.54

(362), Y6.57(365), D6.58(366), K(370), M(371), N(372), K(373), L(374), I(375), K(376), and F7.35(379) of the CB$_1$ receptor, and the directing moiety prevents binding of the compound to one more amino acid residues selected from the group consisting of P6.50(358), A6.53(361), I6.54(362), Y6.57(365), M(371), F7.35(379), C7.38(382), and S7.39 (383) of the CB$_1$ receptor.

In some embodiments, the compound has the Formula I:

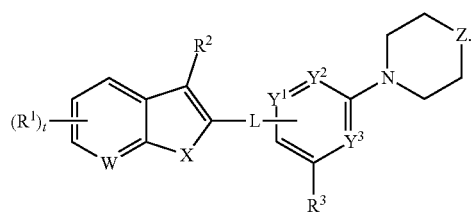
(I)

For compounds of Formula I:
R$^1$ is selected from the group consisting of halo, cyano, nitro, and acetyl;
R$^2$ is selected from the group consisting of C$_{1-12}$ alkyl, C$_{0-4}$ alkyl-C$_{3-8}$ cycloalkyl, and C$_{0-4}$ alkyl-C$_{6-10}$ aryl,
R$^3$ is selected from the group consisting of H, C$_3$-C$_{12}$ alkyl, C$_3$-C$_8$ cycloalkyl, 4- to 8-membered heterocyclyl, C$_6$-C$_{10}$ aryl, and 5- to 10-membered heteroaryl;
W is selected from the group consisting of N and CR$^{1a}$, wherein R$^{1a}$ is selected from the group consisting of H and R$^1$;
X is selected from the group consisting of O, C=O, and NR$^4$, wherein R$^4$ is selected from the group consisting of H and C$_{1-6}$ alkyl;
Y$^1$, Y$^2$, and Y$^3$ are independently selected from the group consisting of N and CH;
Z is selected from the group consisting of O, CH$_2$, and NR$^4$, wherein R$^4$ is selected from the group consisting of H and C$_{1-6}$ alkyl;
subscript t is 0 when W is CR$^{1a}$ and R$^{1a}$ is R$^1$;
subscript t is 1 when W is N or when W is CR$^{1a}$ and R$^{1a}$ is H; and
L is selected from the group consisting of

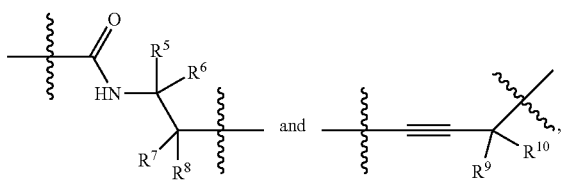

wherein
R$^5$, R$^6$, R$^7$, and R$^8$ are independently selected from the group consisting of H and OH, provided that at least one of R$^5$ and R$^6$ is H and at least one of R$^7$ and R$^8$ is H, or
one of R$^5$ and R$^6$ is taken together with one of R$^7$ and R$^8$ to form a 5- to 6-membered saturated carbocyclic or heterocyclic group, or
R$^5$ and R$^7$ are absent and R$^6$ and R$^8$ are taken together to form a 5- to 6-membered unsaturated carbocyclic or heterocyclic group, and R$^9$ and R$^{10}$ are independently selected from the group consisting of H and OH, provided that at least of R$^9$ and R$^{10}$ is H, and;
provided that if R$^2$ is C$_{1-12}$ alkyl, R$^5$, R$^6$, R$^7$, and R$^8$ are H, and Y$^1$, Y$^2$, and Y$^3$ are CH, then R$^3$ is selected from the group consisting of C$_3$-C$_{12}$ alkyl, C$_3$-C$_8$ cycloalkyl, 4- to 8-membered heterocyclyl, C$_6$-C$_{10}$ aryl, and 5- to 10-membered heteroaryl.

In some embodiments, the compound has the formula:

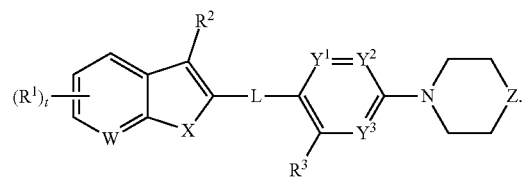

In some embodiments, the compound has the formula:

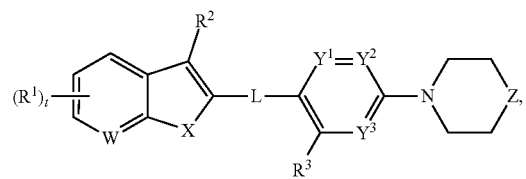

wherein L is selected from the group consisting of

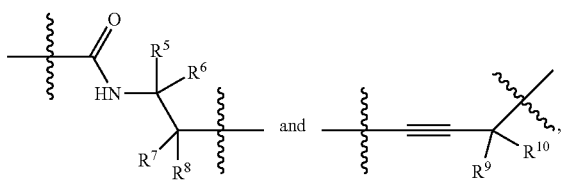

wherein R$^5$, R$^6$, R$^7$, and R$^8$ are independently selected from the group consisting of H and OH, provided that at least one of R$^5$ and R$^6$ is H and at least one of R$^7$ and R$^8$ is H, and
R$^9$ and R$^{10}$ are independently selected from the group consisting of H and OH, provided that at least of R$^9$ and R$^{10}$ is H.

In some embodiments, the compound has the formula:

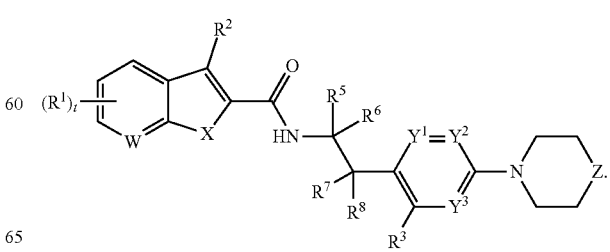

In some embodiments, the compound has the formula:

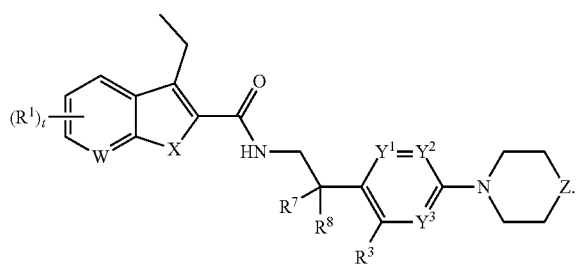

In some embodiments, the compound has a formula selected from the group consisting of:

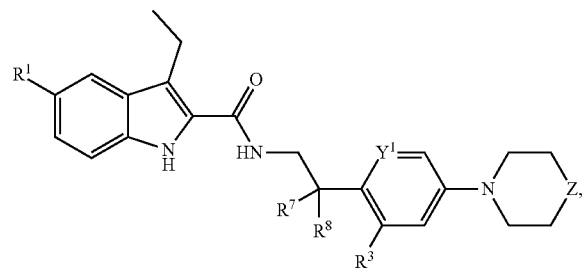

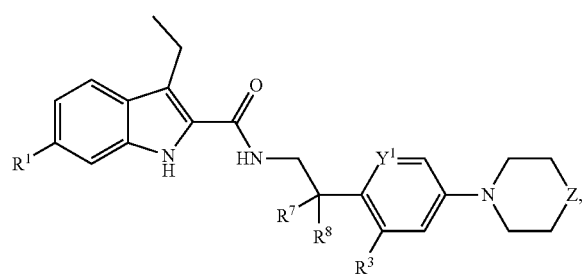

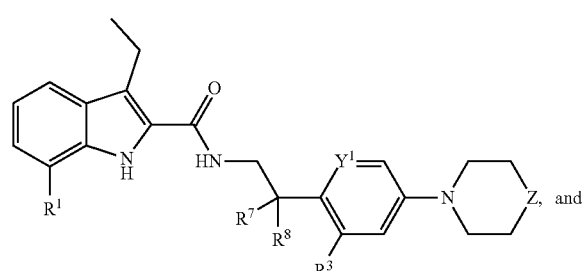

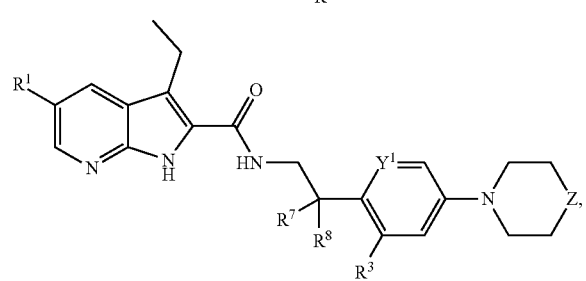

or a pharmaceutically acceptable salt thereof, wherein $R^1$ is selected from the group consisting of Cl and F; and $R^3$ is selected from the group consisting of H, $C_3$-$C_8$ cycloalkyl, and 4- to 8-membered heterocyclyl.

In some embodiments, the compound is selected from the group consisting of:

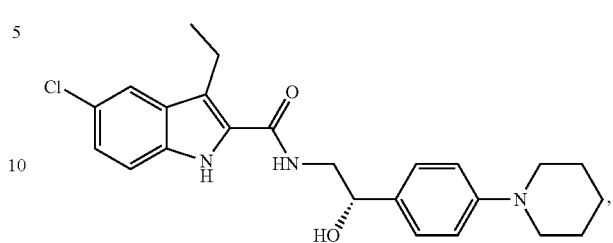

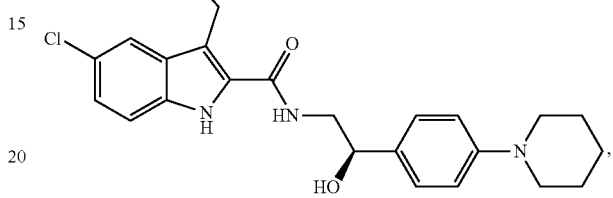

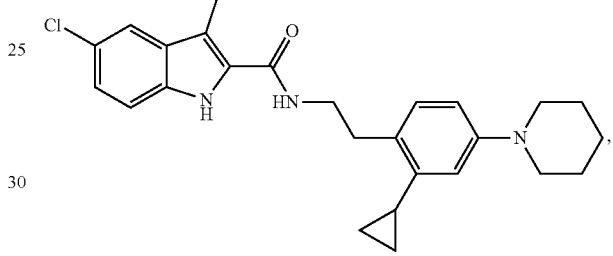

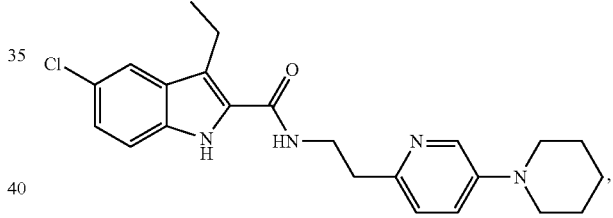

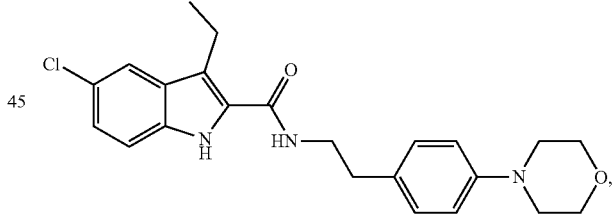

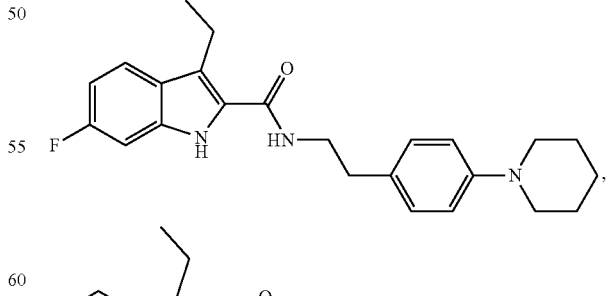

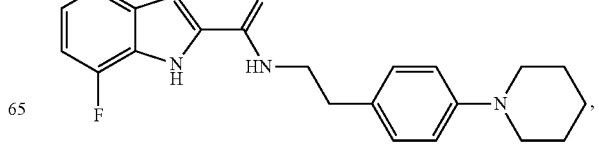

-continued

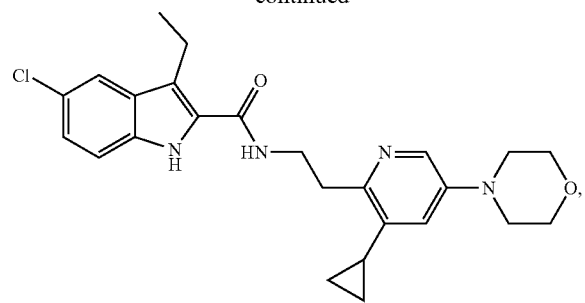

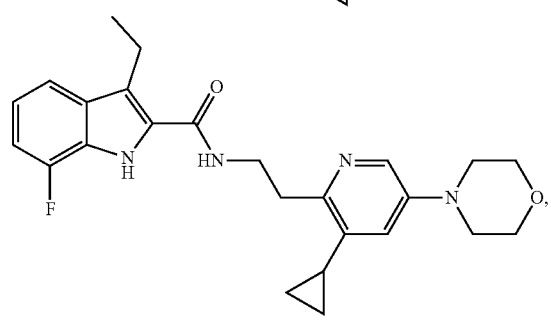

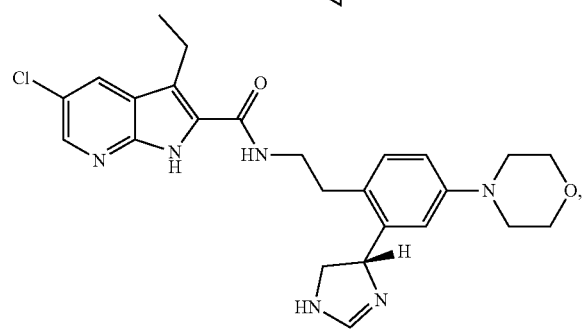

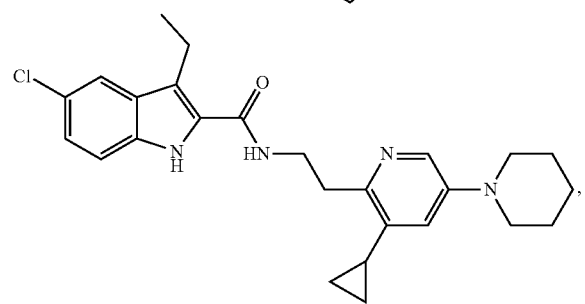

and pharmaceutically acceptable salts thereof.

In some embodiments, the compound is selected from the group consisting of:

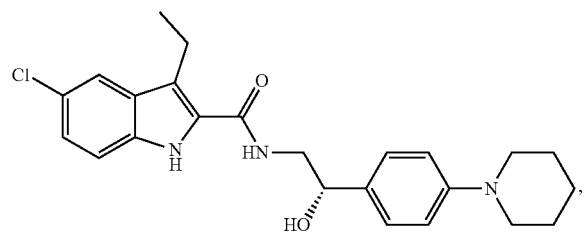 [SMILES: CCc1c(C(=O)NC[C@@H](O)c2ccc(N3CCCCC3)cc2)[nH]c2ccc(Cl)cc12]

(S)-5-chloro-3-ethyl-N-(2-hydroxy-2-(4-(piperidin-1-yl)phenyl)ethyl)-1H-indole-2-carboxamide;

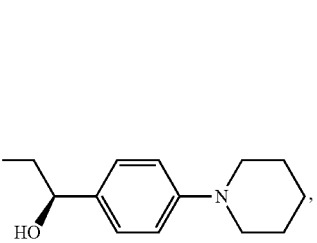

(R)-5-chloro-3-ethyl-N-(2-hydroxy-2-(4-(piperidin-1-yl)phenyl)ethyl)-1H-indole-2-carboxamide;

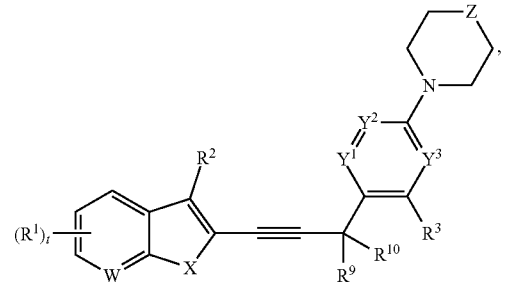

5-chloro-N-(2-cyclopropyl-4-(piperidin-1-yl)phenethyl)-3-ethyl-1H-indole-2-carboxamide;

and pharmaceutically acceptable salts thereof.

In some embodiments, the compound has the formula

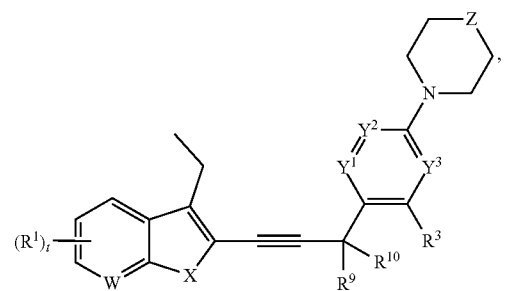

or a pharmaceutically acceptable salt thereof.

In some embodiments, the compound has the formula

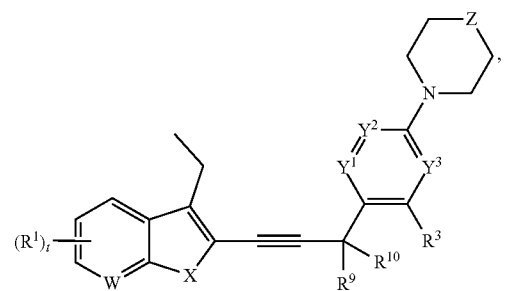

or a pharmaceutically acceptable salt thereof.

In some embodiments, the compound has the formula:

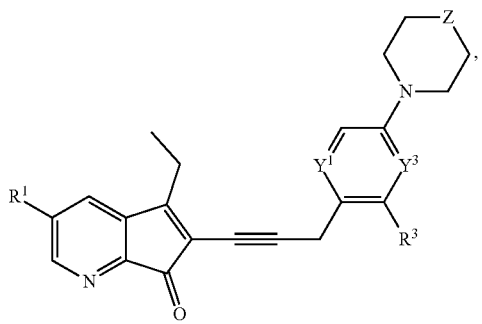

or a pharmaceutically acceptable salt thereof, wherein
R$^1$ is selected from the group consisting of Cl and F; and
R$^3$ is selected from the group consisting of H, C$_3$-C$_8$ cycloalkyl, and 4- to 8-membered heterocyclyl.

In some embodiments, the compound is selected from the group consisting of:

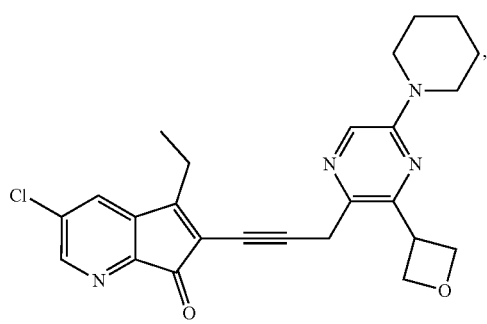

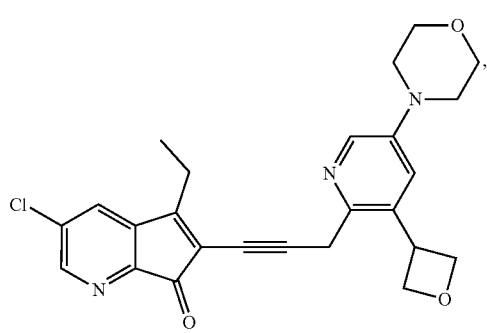

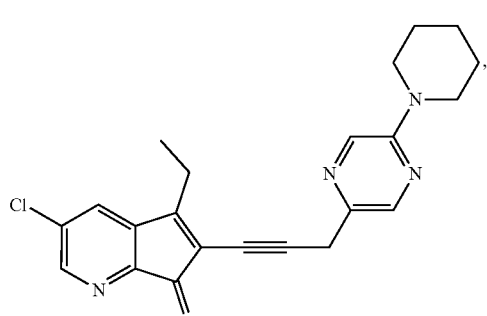

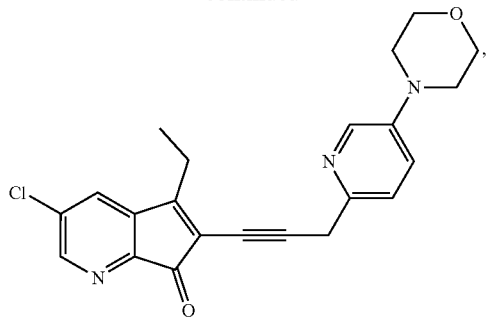

and pharmaceutically acceptable salts thereof.

In some embodiments, the compound has the formula:

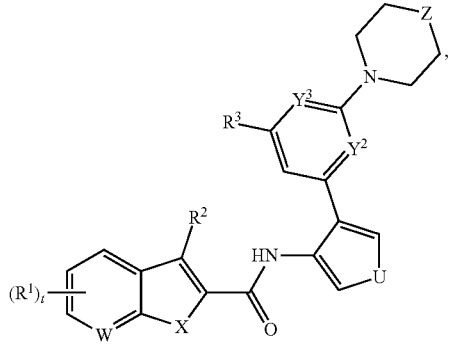

or a pharmaceutically acceptable salt thereof, wherein U is selected from the group consisting of S and O.

In some embodiments, the compound has the formula:

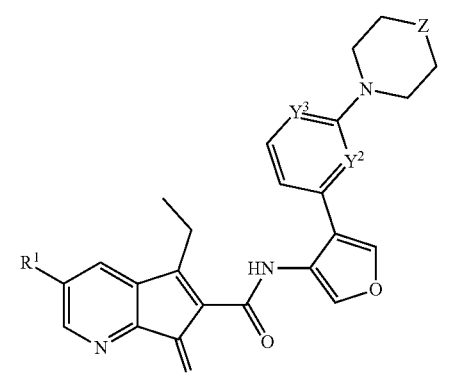

or a pharmaceutically acceptable salt thereof.

In some embodiments, the compound is selected from the group consisting of:

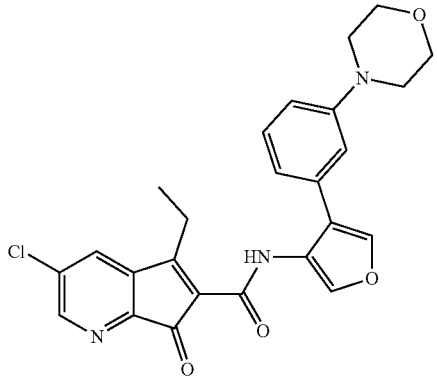

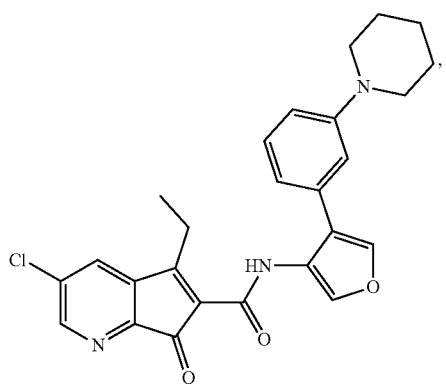

and pharmaceutically acceptable salts thereof.

IV. Methods of Making Compounds

In a related aspect, the invention provides a method of making compounds having a $CB_1$ receptor-binding moiety and a directing moiety as described herein. In some embodiments, the invention provides methods of making compounds of formula II:

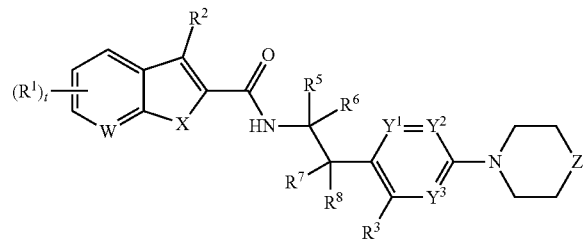

(II)

In some embodiments, the methods for making compounds of formula II include forming a reaction containing an acid of formula III and an amine of formula IV under conditions sufficient to form a compound of formula II.

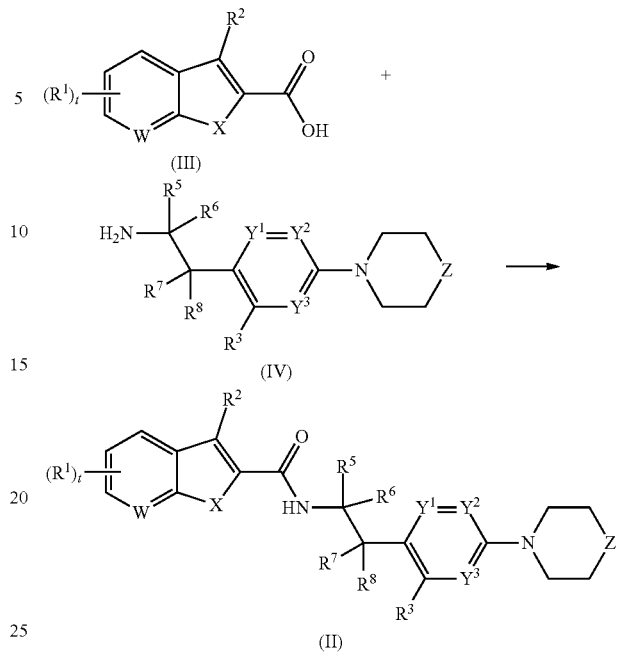

In some embodiments, $R^5$, $R^6$, $R^7$, and $R^8$ of compound IV are H. In some embodiments, the methods for making the compounds of the invention include contacting an aldehyde IVa with a cyclic amine under conditions sufficient to form a compound of formula IVb and converting the compound of formula IVb to a compound of formula IVc. For compounds of formula IVa and formula IVb, $LG^1$ and $LG^2$ are leaving groups that are suitable for displacement with reactants to form compounds of formula IVb and IVc. For example, $LG^1$ and $LG^2$ can be, but are not limited to, halogens (such as fluoride, chloride, bromide, or iodide), a tosylate, a triflate, a mesylate, or the like. Formation of compounds IVb and IVc can be promoted using catalysts such as acids, bases, and transition metals, among others. In certain embodiments, a compound of formula IVb is combined with a boronic acid, a palladium source such as palladium acetate or the like, and a ligand such as tricyclohexylphosphine, triphenylphosphine, or the like, under conditions sufficient to form a compound of Formula IVc. In some embodiments, a compound of formula IVc is contacted with diazomethane under conditions sufficient to form an olefin of formula IVd, which is reduced to form an amine of formula IVe. Amines of formula IVe can be reacted with acids of formula III to provide the compounds of the invention.

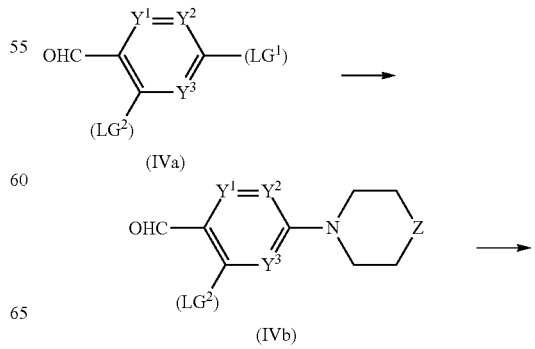

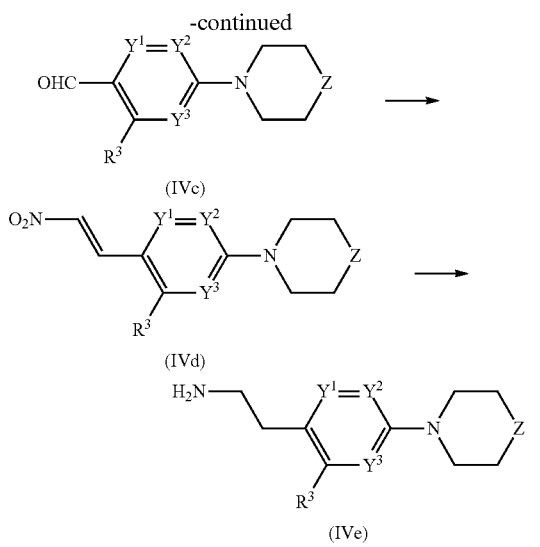

In some embodiments, $R^5$ and $R^6$ of compound IV are H and $R^7$ or $R^8$ of compound IV is OH. In some embodiments, the methods for making the compounds of the invention include forming a reaction mixture contacting an epoxide IVf with a protected amine under conditions sufficient to form an amino-alcohol of formula IVg. The epoxide can be reacted asymmetrically so as to provide a desired enantiomer of the amino-alcohol. Stereoselective epoxide opening can be conducted, for example, using a metal-salen catalyst such as a cobalt-salen complex. For compounds of formula IVf and formula IVg, $LG^3$ is a suitable leaving group that can be displaced with a cyclic amine to provide compounds of formula IVh. $LG^3$ can be, but is not limited to, a halogen (such as fluoride, chloride, bromide, or iodide), a tosylate, a triflate, a mesylate, or the like. For compounds of formula IVg and IVh, PG is a protecting group. A number of amine protecting groups are known in the art, as described, for example, in *Protective Groups in Organic Synthesis*, 4$^{th}$ Ed. (T. W. Greene and P. G. M. Wuts, John Wiley & Sons, New York, 2006). In some embodiments, acid-labile protecting groups such as tert-butoxycarbonyl are used in the methods of the invention. Protected amines of formula IVh can be deprotected and reacted with acids of formula III to provide further compounds of the invention.

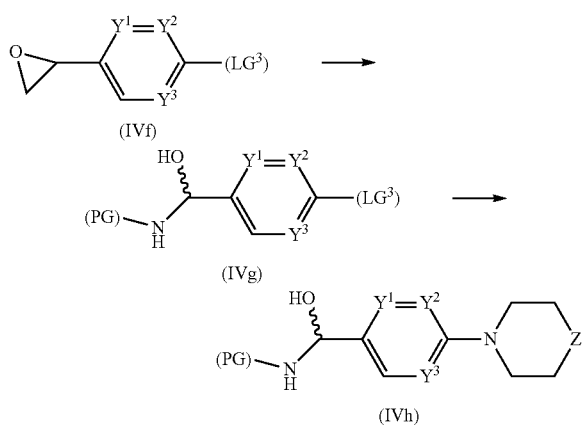

In some embodiments, $R^5$ and $R^7$ of Compound IV are absent and $R^6$ and $R^8$ are taken together to form a 5- to 6-membered unsaturated heterocyclic group. In some embodiments, the methods for making the compounds of the invention include reducing an azido-heterocycle of formula IVi to form an amino-heterocycle of formula IVj and subsequent cross-coupling with boronate ester IVk to form an amine according to formula IVl.

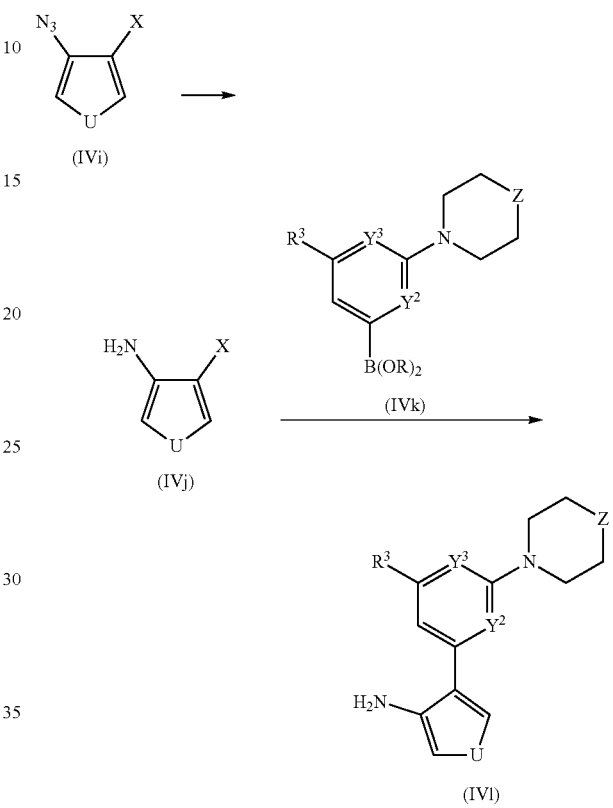

The starting materials and reagents used in preparing the compounds of the invention are either available from commercial suppliers or are prepared by methods known to those skilled in the art following procedures set forth in references such as Fieser and Fieser's *Reagents for Organic Synthesis*, Volumes 1-17 (John Wiley and Sons, 1991); Rodd's *Chemistry of Carbon Compounds*, Volumes 1-5 and Supplementals (Elsevier Science Publishers, 1989); *Organic Reactions*, Volumes 1-40 (John Wiley and Sons, 1991), March's *Advanced Organic Chemistry*, (John Wiley and Sons, 4th Edition) and Larock's *Comprehensive Organic Transformations* (VCH Publishers Inc., 1989).

The starting materials and the intermediates of the reaction can be isolated and purified if desired using conventional techniques including, but not limited to, filtration, distillation, crystallization, chromatography and the like. Such materials can be characterized using conventional means, including measuring physical constants and obtaining spectral data.

Unless specified to the contrary, the reactions described herein take place at atmospheric pressure over a temperature range of from about −78° C. to about 150° C. For example, reactions can be conducted at from about 0° C. to about 125° C., or at about room (or ambient) temperature, e.g., about 20° C. In some embodiments, reactions are conducted at about 0° C., 20° C., 25° C., 90° C., 100° C., 110° C., or 120° C. In some embodiments, reactions are conducted starting at a temperature of about 0° C., and allowed to warm to a temperature of about 20° C. or about 25° C. One of skill in the art will appreciate that various modifications to the procedures described herein can be made.

V. Pharmaceutical Compositions

In another aspect, the invention provides a pharmaceutical composition comprising a compound of the invention as described above and one or more pharmaceutically acceptable excipients.

The pharmaceutical compositions can be prepared by any of the methods well known in the art of pharmacy and drug delivery. In general, methods of preparing the compositions include the step of bringing the active ingredient into association with a carrier containing one or more accessory ingredients. The pharmaceutical compositions are typically prepared by uniformly and intimately bringing the active ingredient into association with a liquid carrier or a finely divided solid carrier or both, and then, if necessary, shaping the product into the desired formulation. The compositions can be conveniently prepared and/or packaged in unit dosage form.

The pharmaceutical compositions can be in the form of a sterile injectable aqueous or oleaginous solutions and suspensions. Sterile injectable preparations can be formulated using non-toxic parenterally-acceptable vehicles including water, Ringer's solution, and isotonic sodium chloride solution, and acceptable solvents such as 1,3-butanediol. In addition, sterile, fixed oils are conventionally employed as a solvent or suspending medium. For this purpose any bland fixed oil can be employed including synthetic mono- or diglycerides. In addition, fatty acids such as oleic acid find use in the preparation of injectables.

Aqueous suspensions contain the active materials in admixture with excipients suitable for the manufacture of aqueous suspensions. Such excipients include, but are not limited to: suspending agents such as sodium carboxymethylcellulose, methylcellulose, oleagino-propylmethylcellulose, sodium alginate, polyvinyl-pyrrolidone, gum tragacanth and gum acacia; dispersing or wetting agents such as lecithin, polyoxyethylene stearate, and polyethylene sorbitan monooleate; and preservatives such as ethyl, n-propyl, and p-hydroxybenzoate.

Oily suspensions can be formulated by suspending the active ingredient in a vegetable oil, for example, arachis oil, olive oil, sesame oil or coconut oil, or in a mineral oil such as liquid paraffin. The oily suspensions can contain a thickening agent, for example beeswax, hard paraffin or cetyl alcohol. These compositions can be preserved by the addition of an anti-oxidant such as ascorbic acid.

Dispersible powders and granules (suitable for preparation of an aqueous suspension by the addition of water) can contain the active ingredient in admixture with a dispersing agent, wetting agent, suspending agent, or combinations thereof. Additional excipients can also be present.

The pharmaceutical compositions of the invention can also be in the form of oil-in-water emulsions. The oily phase can be a vegetable oil, for example olive oil or arachis oil, or a mineral oil, for example liquid paraffin or mixtures of these. Suitable emulsifying agents can be naturally-occurring gums, such as gum acacia or gum tragacanth; naturally-occurring phospholipids, such as soy lecithin; esters or partial esters derived from fatty acids and hexitol anhydrides, such as sorbitan monooleate; and condensation products of said partial esters with ethylene oxide, such as polyoxyethylene sorbitan monooleate.

Pharmaceutical compositions containing compounds of the invention can also be in a form suitable for oral use. Suitable compositions for oral administration include, but are not limited to, tablets, troches, lozenges, aqueous or oily suspensions, dispersible powders or granules, emulsions, hard or soft capsules, syrups, elixirs, solutions, buccal patches, oral gels, chewing gums, chewable tablets, effervescent powders, and effervescent tablets. Compositions for oral administration can be formulated according to any method known to those of skill in the art. Such compositions can contain one or more agents selected from sweetening agents, flavoring agents, coloring agents, antioxidants, and preserving agents in order to provide pharmaceutically elegant and palatable preparations.

Tablets generally contain the active ingredient in admixture with non-toxic pharmaceutically acceptable excipients, including: inert diluents, such as cellulose, silicon dioxide, aluminum oxide, calcium carbonate, sodium carbonate, glucose, mannitol, sorbitol, lactose, calcium phosphate, and sodium phosphate; granulating and disintegrating agents, such as corn starch and alginic acid; binding agents, such as polyvinylpyrrolidone (PVP), cellulose, polyethylene glycol (PEG), starch, gelatin, and acacia; and lubricating agents such as magnesium stearate, stearic acid, and talc. The tablets can be uncoated or coated, enterically or otherwise, by known techniques to delay disintegration and absorption in the gastrointestinal tract and thereby provide a sustained action over a longer period. For example, a time delay material such as glyceryl monostearate or glyceryl distearate can be employed. Tablets can also be coated with a semi-permeable membrane and optional polymeric osmogents according to known techniques to form osmotic pump compositions for controlled release.

Compositions for oral administration can be formulated as hard gelatin capsules wherein the active ingredient is mixed with an inert solid diluent (such as calcium carbonate, calcium phosphate, or kaolin), or as soft gelatin capsules wherein the active ingredient is mixed with water or an oil medium (such as peanut oil, liquid paraffin, or olive oil).

Compounds of the invention can also be administered topically as a solution, ointment, cream, gel, suspension, eye-drops, and the like. Still further, transdermal delivery of compounds of the invention can be accomplished by means of iontophoretic patches and the like. The compound can also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials include cocoa butter and polyethylene glycols.

In some embodiments, a compound of the invention is administered via intraperitoneal injection. In some embodiments, the compound is administered orally.

In a related aspect, the invention provides a kit having a pharmaceutical composition as described above and instructions for use.

VI. In Vitro (In Silico) Methods

In a related aspect, the invention provides a computer program for searching a compound database comprising a plurality of entries, each entry corresponding to a surface representation of a TMH6 and TMH7 binding pocket of the CB1 receptor and CWXP hinge region of the CB1 receptor; said program including a means for calculating the average distance between the surfaces of the TMH6 and TMH7 binding pocket, the CWXP hinge region and a target compound; and comparing the average distances.

III.A ORG27569 Binding and Signaling at the Cannabinoid $CB_1$ Receptor.

ORG27569 High Binding Mode

Our molecular dynamics (MD) simulations have shown that ORG27569 can enter the cannabinoid $CB_1$ receptor via the lipid bilayer by inserting between transmembrane helix (TMH) 6 and TMH7. ORG27569 enters "High," near the extracellular ends of these helices and the extracellular (EC)-3 loop closes down over ORG27569 (see FIG. 2A). This produces a change in the intracellular (IC) domains of the receptor (movement of the IC end of TMH7 away from the IC end of TMH2) that is consistent with a beta-arrestin signaling event. {Liu, J. J., Horst, R., Katritch, V., Stevens, R. C., and Wuthrich, K. (2012) "Biased signaling pathways in beta2-adrenergic receptor characterized by 19F-NMR." *Science* 335, 1106-1110} The IC opening that is formed in our simulations is large enough to accommodate docking of beta-arrestin with CB1. These results are consistent with the report that ORG27569 can signal via beta-arrestin 1. {Ahn, K. H., Mahmoud, M. M., Shim, J. Y., and Kendall, D. A. (2013) "Distinct roles of beta-arrestin 1 and beta-arrestin 2 in ORG27569-induced biased signaling and internalization of the cannabinoid receptor 1 (CB1)." *J Biol Chem* 288, 9790-9800}

Figure 2A:
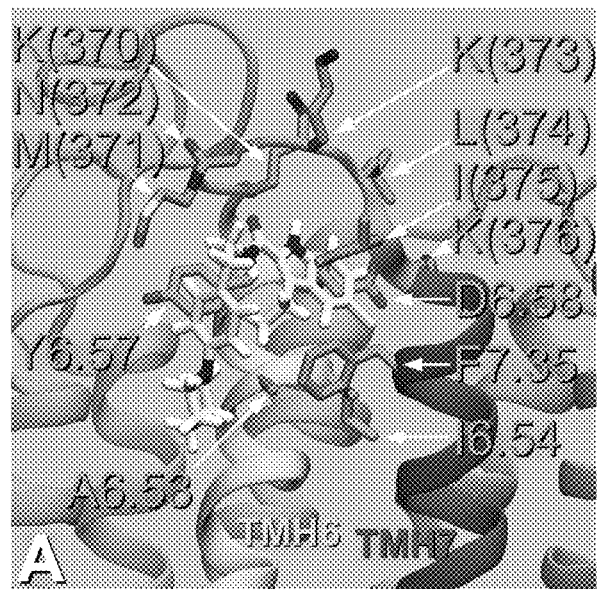
FIG. 2A shows ORG27569 (yellow) inserted between the EC ends of TMH6(pink)/TMH7(purple) with the EC-3 loop interacting with the ligand. Residues with which ORG27569 interacts are colored green here. The high entry of ORG27569 results in beta-arrestin biased signaling.

In this High binding mode, the residues lining the binding pocket between TMH6 and TMH7 and including the EC-3 loop are defined by A6.53(361), I6.54(362), Y6.57(365), D6.58(366), K(370), M(371), N(372), K(373), L(374), I(375), K(376), F7.35(379) as shown in FIG. 2A. The residues are in contact with ORG for 890 ns in the molecular dynamics simulation while ORG is bound. Prior to the EC-3 loop descending down onto the indole NH and the amide carbonyl oxygen of ORG, the predominant interaction sites were the TMH6-7 residues listed above for the first 93 ns of the bound state. Measurements below were for the entire 890 ns of binding. Average distances from binding residue C-alpha (CA) carbons to ORG27569 are listed in Table 1.

TABLE 1

| Indole N1 Nitrogen | | |
|---|---|---|
| TMH6 Y6.57 | C-alpha = 5.9 Å (min = 4.4 Å, max = 9.1 Å) | SD = 0.7 Å |
| EC3 K(370) | C-alpha = 5.7 Å (min = 3.5 Å, max = 11.5 Å) | SD = 1.3 Å |
| EC3 K(373) | C-alpha = 5.6 Å (min = 4.1 Å, max = 10.7 Å) | SD = 1.0 Å |
| EC3 L(374) | C-alpha = 5.0 Å (min = 3.5 Å, max = 10.6 Å) | SD = 1.3 Å |
| Amide Carbonyl Carbon | | |
| EC3 M(371) | C-alpha = 6.7 Å (min = 4.3 Å, max = 12.9 Å) | SD = 1.6 Å |
| EC3 N(372) | C-alpha = 7.0 Å (min = 4.5 Å, max = 14.7 Å) | SD = 1.9 Å |
| Indole C3 Carbon (where the ethyl moiety is attached) | | |
| TMH6 A6.53 | C-alpha = 6.8 Å (min = 5.1 Å, max = 9.1 Å) | SD = 0.8 Å |
| EC3 I (375) | C-alpha = 5.0 Å (min = 3.9 Å, max = 8.5 Å) | SD = 0.8 Å |
| TMH7 F7.35 | C-alpha = 7.5 Å (min = 5.8 Å, max = 10.7 Å) | SD = 0.8 Å |
| Indole C5 Carbon (where chlorine is attached) | | |
| TMH6 I6.54 | C-alpha = 5.2 Å (min = 3.9 Å, max = 8.7 Å) | SD = 0.8 Å |

TABLE 1-continued

| TMH6 D6.58 | C-alpha = 5.1 Å (min = 4.1 Å, max = 8.3 Å) | SD = 0.6 Å |
|---|---|---|
| EC3 K(376) | C-alpha = 4.5 Å (min = 3.4 Å, max = 7.8 Å) | SD = 0.7 Å |

The overall shape of the ligand when bound is a low energy, folded conformation. The center dihedral conferring the ability to fold or straighten is located between the amide group and the phenyl ring. When bound in the High binding mode, the dihedral is in a gauche conformation. The average distance between the indole C3 position and the piperidine nitrogen is 7.1 Å with a SD=0.5 Å.

ORG27569 Forced Low Binding Mode

Figure 2B:
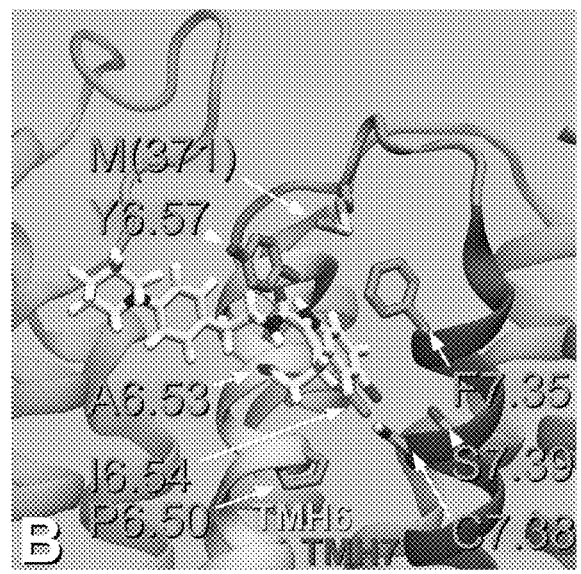
FIG. 2B shows that if ORG27569 is forced to enter one turn lower in the TMH6/TMH7 interface, the set of interacting residues (green) includes the proline (P6.50(358)) of the CWXP flexible hinge motif. Interaction with this flexible hinge region is associated with G-protein activation.

We have found that forcing ORG27569 to enter the $CB_1$ receptor one turn lower on TMH6 and TMH7 results in a conformational change in the IC domains of the receptor that lead to breakage of the R3.50(214)/D6.30(338) ionic lock—a hallmark of G-Protein activation. {Hurst, D. P., Grossfield, A., Lynch, D. L., Feller, S., Romo, T. D., Gawrisch, K., Pitman, M. C., and Reggio, P. H. (2010) "A lipid pathway for ligand binding is necessary for a cannabinoid G protein-coupled receptor." *J Biol Chem* 285, 17954-17964} The residues lining the "Low" binding mode pocket between TMH6 and 7 are defined by P6.50(358), A6.53 (361), I6.54(362), Y6.57(365), M(371), F7.35(379), C7.38 (382), and S7.39(383) as shown in FIG. 2B. P6.50(358) is part of the highly conserved CWXP motif in Class A GPCRs. Interaction with this flexible hinge region is associated with G-protein activation. The residues are in contact with ORG for 105 ns (entire simulation time) in the MD simulation. During this period defined by the Low binding mode, the average distances from binding residue CA carbons to ORG27569 are listed in Table 2.

TABLE 2

| Indole C5 Carbon (where chlorine is attached) | | |
|---|---|---|
| TMH6 P6.50 | C-alpha = 4.8 Å (min = 3.9 Å, max = 6.6 Å) | SD = 0.5 Å |
| TMH6 I6.54 | C-alpha = 4.9 Å (min = 4.0 Å, max = 6.0 Å) | SD = 0.4 Å |
| TMH7 F7.35 | C-alpha = 4.4 Å (min = 3.7 Å, max = 5.5 Å) | SD = 0.3 Å |
| TMH7 C7.38 | C-alpha = 5.8 Å (min = 5.2 Å, max = 7.7 Å) | SD = 0.4 Å |
| TMH7 S7.39 | C-alpha = 6.2 Å (min = 4.8 Å, max = 8.2 Å) | SD = 0.5 Å |
| Indole C3 Carbon (where the ethyl moiety is attached) | | |
| TMH6 Y6.53 | C-alpha = 5.3 Å (min = 4.7 Å, max = 6.5 Å) | SD = 0.3 Å |
| Indole N1 Nitrogen | | |
| TMH6 Y6.57 | C-alpha = 6.1 Å (min = 4.7 Å, max = 9.4 Å) | SD = 0.6 Å |
| EC3 M(371) | C-alpha = 8.1 Å (min = 6.7 Å, max = 9.9 Å) | SD = 0.6 Å |

The overall shape of ORG is extended with the central dihedral in trans that confers folded versus extended shapes. When the molecule is unfolded, or straight, the average distance between the indole C3 position and the piperidine nitrogen is 10.8 Å with a SD=0.4 Å.

We have shown previously for the Cannabinoid CB2 receptor that ligand entry via the lipid bilayer between TMH6 and TMH7 results in activation of CB2. {Hurst, D. P., Grossfield, A., Lynch, D. L., Feller, S., Romo, T. D., Gawrisch, K., Pitman, M. C., and Reggio, P. H. (2010) A lipid pathway for ligand binding is necessary for a cannabinoid G protein-coupled receptor. J Biol Chem 285, 17954-17964}. Here we have found that ORG27569 enters the $CB_1$ receptor from lipid also between TMH6 and TMH7. The entry point is high (top turn of TMH6/TMH7) and the result is a conformational change associated with beta-arrestin biased signaling. Forcing ORG27569 to enter lower, results in the conformational change associated with G-protein signaling. Without wishing to be bound by any particular theory, it is believed that the TMH6/TMH7 interface is a "tunable" port wherein the signal or signals sent from the port are directly related to the height of ligand entry from the lipid bilayer.

A series of molecular dynamics simulations were conducted with a fully hydrated POPC phospholipid bilayer, containing the CB1 receptor and fourteen ORG27569 molecules (seven in each leaflet). ORG27569 molecules interacted freely with the lipid bilayer and CB1 during the simulations.

The "bent" series of ORG27569 analogs were designed from studying the interactions of ORG27569 found in our molecular dynamics simulations. ORG27569, due to inherent lipophilicity, was observed to partition into the lipid bilayer readily from water. The lipid bilayer's unique property of hydrophilic headgroups and a hydrophobic core can orient lipophilic ligands and present specific conformations of such ligands to a receptor with lipid facing entry portals such as the CB1 and CB2 receptors, rhodopsin, and the $S1P_1$ receptors. The exposed hydrophilic carbonyl oxygen and indole N—H in ORG27569 were observed to interact mainly with phospholipid head groups. Simultaneously, the indole 5 position chlorine and 3 position ethyl substituent preferred to interact with the hydrophobic core of the lipid bilayer, forcing an orientation of the indole that was perpendicular to the plane of the lipid bilayer. The phenyl piperidine tail of ORG27569 also preferred to interact with the hydrophobic core of the bilayer. We found that taking all these interactions into consideration, ligand design should promote and not interfere with this typical orientation of ORG27569 in the lipid bilayer.

ORG27569 binding to the TMH6/TMH7 interface of CB1 yielded showed that the indole ring's orientation in the bound conformation was very similar to the unbound conformation in the lipid bilayer. We already had confirmed that a folded conformation of ORG27569 was the lowest energy conformation, and the observations from the MD simulations demonstrated that the folded conformation was preferred when the ligand bound to the receptor. At the TMH6/TMH7 site, the fused ring structure of ORG27569 has hydrophobic interactions with Y6.57 and I7.31 which flank the sides of the ligand and F7.35(383) which forms the floor of the binding site. The substituents on the indole ring and the carboxamide group have hydrogen bonding interactions with EC-3 loop residue backbone atoms (particularly an N(372) N—H interaction with the carboxamide oxygen on ORG27569). In the folded conformation, the piperidine ring of the ligand interacts with P6.50 and A6.53, while the ligand phenyl ring packs against the ligand.

"Bent" compounds of the present invention were designed such that the hydrophilic regions of the ligand were able to interact with phospholipid headgroups in the unbound state and the hydrophilic regions of the CB1 receptor in the bound state, without requiring a major ligand conformational change upon binding. For the "bent" compounds described here, a scaffold was sought that rigidified the molecule into a permanently folded state such that the hydrophilic carbonyl oxygen and indole N—H were directed away from the phenyl piperidine tail. Insertion of a cyclic moiety, such as furan ring, into the ethyl linker between the amide and phenyl groups created a more rigid folded scaffold. Attaching the carboxamide group at the furan 3 position and the phenyl piperidine tail at the furan 4 provided a permanently folded compound as shown in Formula A.

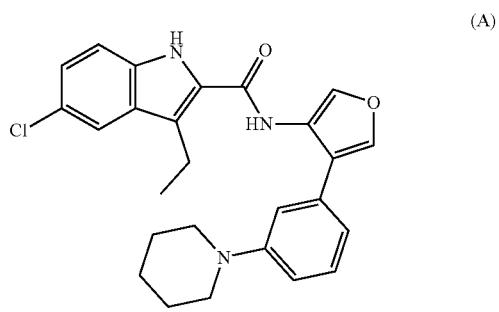 [SMILES: CCc1c(C(=O)Nc2cocc2-c2cccc(N3CCCCC3)c2)[nH]c2ccc(Cl)cc12]

(A)

In certain embodiments, the invention provides a method of identifying a selective agonist of the beta-arrestin pathway over the G-protein pathway. Thus in another group of embodiments, the invention provides a method of identifying a selective agonist of the beta-arrestin pathway over the G-protein pathway comprising: creating a query using one or more descriptors that each represent the surface of a TMH6 and TMH7 binding pocket of the CB1 receptor and a CWXP hinge region of the CB1 receptor; and identifying compounds where the smallest average distance between the TMH6 surface and the compound is from about 0.2 angstroms (Å) to about 16 Å and the average distance between the surfaces of the CWXP hinge region and the compound is from about 0.8 Å to about 12 Å. In some embodiments, the method includes identifying compounds where the smallest average distance between the TMH6 surface and the compound is from about 0.6 Å to about 14.7 Å and the average distance between the surfaces of the CWXP hinge region and the compound is from about 1.1 Å to about 9.9 Å. In some embodiments, the method includes identifying compounds where the smallest average distance between the TMH6 surface and the compound is from about 3.4 Å to about 14.7 Å. In some embodiments, the method includes identifying compounds where the average distance between the surfaces of the CWXP hinge region and the compound is from about 3.7 Å to about 9.9 Å. In some embodiments, the method includes identifying compounds where the smallest average distance between the TMH6 surface and the compound is from about 0.6 Å to about 3.0 Å. In some embodiments, the method includes identifying compounds where the average distance between the surfaces of the CWXP hinge region and the compound is from about 1.1 Å to about 2.8 Å.

In some embodiments, determining the smallest average distance between the TMH6 surface and the compound includes determining the distance between the bridge carbon nearest to the N1 nitrogen of the indole moiety in the compound and the C-beta atom of Y6.57(365) in TMH6. In some embodiments, determining the average distance between the surfaces of the CWXP hinge region and the compound includes determining the distance between C4 carbon atom of the indole moiety in the compound and the C-alpha carbon of P6.50(358) in TMH6.

In some embodiments, the method includes identifying a compound that binds in a non-covalent manner with one or more $CB_1$ receptor amino acid residues selected from the group consisting of A6.53(361), I6.54(362), Y6.57(365), D6.58(366), K(370), M(371), N(372), K(373), L(374), I(375), K(376), and F7.35(379); and determining that the compound does not bind to one more $CB_1$ receptor amino acid residues selected from the group consisting of P6.50 (358), A6.53(361), I6.54(362), Y6.57(365), M(371), F7.35 (379), C7.38(382), and S7.39(383).

In some embodiments, identifying a compound that binds in a non-covalent manner with one or more $CB_1$ receptor amino acid residues selected from the group consisting of A6.53(361), I6.54(362), Y6.57(365), D6.58(366), K(370), M(371), N(372), K(373), L(374), I(375), K(376), and F7.35 (379) includes determining that the compound does not affect GTP-gamma-S binding in cells. In some embodiments, identifying a compound that binds in a non-covalent manner with one or more $CB_1$ receptor amino acid residues selected from the group consisting of A6.53(361), I6.54 (362), Y6.57(365), D6.58(366), K(370), M(371), N(372), K(373), L(374), I(375), K(376), and F7.35(379) includes determining that the compound does promotes pERK production in cells.

VII. Methods of Treatment

In another aspect, the invention provides a method of inhibiting a pathway modulated in part by $CB_1$ receptor activity comprising the step of contacting a cell with a compound of the invention as described above.

In another aspect, the invention provides a method of treating a condition or disorder mediated in part by $CB_1$ receptor activity in a patient in need thereof, the method comprising administering to the patient an effective amount of a compound of the invention as described above. The methods of the invention can be used to treat a number of conditions including, but not limited to, metabolic syndromes such as type 2 diabetes, dyslipidemia, and obesity; eating disorders; cardiovascular diseases or disorders such as hypertension, congestive heart failure, cardiac hypertrophy, peripheral artery disease, atherosclerosis, stroke, myocardial infarction, and cardiotoxicity associated with chemotherapy; fatty liver disease (steatohepatitis) and non-alcoholic fatty liver disease; kidney disease; diseases or disorders characterized by an addiction component such as smoking addiction or withdrawal, alcohol addiction or withdrawal, and drug addiction or withdrawal; bone diseases or disorders such as osteoporosis, Paget's disease of bone, and bone cancer; breast cancer; inflammatory diseases or autoimmune diseases such as rheumatoid arthritis, inflammatory bowel disease, and psoriasis; psychiatric diseases or disorders such as anxiety, mania, schizophrenia; and disorders or diseases associated with memory impairment and/or loss of cognitive function such as Parkinson's disease, Alzheimer's disease, and dementia.

In some embodiments, the cannabinoid-mediated condition is selected from the group consisting of glaucoma, pain, nausea, neurodegeneration, and appetite loss.

The compounds can be administered at any suitable dose in the methods of the invention. In general, the compounds are administered at a dose ranging from about 0.1 milligrams to about 1000 milligrams per kilogram of a subject's body weight (i.e., about 0.1-1000 mg/kg). The dose of a compound can be, for example, about 0.1-1000 mg/kg, or about 1-500 mg/kg, or about 25-250 mg/kg, or about 50-100 mg/kg. The dose can be about 1, 2, 3, 4, 5, 10, 15, 20, 25, 30, 35, 40, 45, 50, 55, 60, 65, 70, 75, 85, 90, 95, 100, 150, 200, 250, 300, 350, 400, 450, 500, 550, 600, 650, 700, 750, 800, 850, 900, 950 or 1000 mg/kg.

The dosages can be varied depending upon the requirements of the patient, the severity of the disorder being treated, and the particular formulation being administered. The dose administered to a patient should be sufficient to result in a beneficial therapeutic response in the patient. The size of the dose will also be determined by the existence, nature, and extent of any adverse side-effects that accompany the administration of the drug in a particular patient. Determination of the proper dosage for a particular situation is within the skill of the typical practitioner. The total dosage can be divided and administered in portions over a period of time suitable to treat to the condition or disorder.

Administration can be conducted for a period of time which will vary depending upon the nature of the particular disorder, its severity and the overall condition of the patient. Administration can be conducted, for example, hourly, every 2 hours, three hours, four hours, six hours, eight hours, or twice daily including every 12 hours, or any intervening interval thereof. Administration can be conducted once daily, or once every 36 hours or 48 hours, or once every month or several months. Following treatment, a patient can be monitored for changes in his or her condition and for alleviation of the symptoms of the disorder. The dosage can either be increased in the event the patient does not respond significantly to a particular dosage level, or the dose can be decreased if an alleviation of the symptoms of the disorder is observed, or if the disorder has been ablated, or if unacceptable side effects are seen with a particular dosage.

A therapeutically effective amount of a compound of the invention can be administered to the subject in a treatment regimen comprising intervals of at least 1 hour, or 6 hours, or 12 hours, or 24 hours, or 36 hours, or 48 hours between dosages. Administration can be conducted at intervals of at least 72, 96, 120, 168, 192, 216, or 240 hours, or the equivalent amount of days. The dosage regimen can consist of two or more different interval sets. For example, a first part of the dosage regimen can be administered to a subject multiple times daily, daily, every other day, or every third day. The dosing regimen can start with dosing the subject every other day, every third day, weekly, biweekly, or monthly. The first part of the dosing regimen can be administered, for example, for up to 30 days, such as 7, 14, 21, or 30 days. A subsequent second part of the dosing regimen with a different interval administration administered weekly, every 14 days, or monthly can optionally follow, continuing for 4 weeks up to two years or longer, such as 4, 6, 8, 12, 16, 26, 32, 40, 52, 63, 68, 78, or 104 weeks. Alternatively, if the disorder goes into remission or generally improves, the dosage may be maintained or kept at lower than maximum amount. If the condition or disorder relapses, the first dosage regimen can be resumed until an improvement is seen, and the second dosing regimen can be implemented again. This cycle can be repeated multiple times as necessary.

Additional active agents or therapies can be co-administered or otherwise combined with the compounds of the present invention. Additional active agents and therapies suitable for use in the methods of the invention include, but are not limited to, compounds used in the treatment of type-2 diabetes and obesity, such as insulin and insulin analogues, dipeptidyl peptidase-4 (DPP-4) inhibitors, glucagon-like peptide-1 analogues, hypoglycemic agents, such as alpha-glucosidase inhibitors, biguanides, sulfonyl ureas, thiazolidinediones, weight loss therapies, such as appetite suppressing agents, serotonin reuptake inhibitors, noradrenaline reuptake inhibitors, $\beta_3$-adrenoceptor agonists, and lipase inhibitors. Compounds used in the treatment of cardiovascular disease and dysfunction can also be used in the methods invention, including, but not limited to, diuretics, angiotensin-converting enzyme (ACE) inhibitors, angiotensin II antagonists, beta-blockers, calcium antagonists, such as nifedipine, HMG-CoA-reductase inhibitors, such as statins, digoxin, aldosterone antagonists, and organic nitrates. Other lipid modulating agents including, but not limited to, fibrates and bile acid-binding resins can be used in the methods of the invention. The compounds of the invention can be used with compounds used to assist smoking cessation including, but not limited to, norepinephrine-dopamine reuptake inhibitors such as bupropion.

Compounds used in the treatment of bone diseases and disorders can be used in the methods of the invention. Such compounds include, but are not limited to anti-resorptive agents such as bisphosphonates, anabolic agents such as parathyroid hormone, RANKL inhibitors such as denosumab; and estrogen replacement and selective estrogen receptor modulators such as raloxifene. Compounds used in the treatment of breast cancer, such as compounds which modulate tubulin polymerization, such as paclitaxel; targeted therapies, such as antibodies against specific cell surface markers on tumor cells, such as antibodies against the HER2 oncoprotein, such as trastuzumab.

Compounds used in the treatment of a disease or disorder with an inflammatory or autoimmune component can be used in the methods of the invention. Such compounds include non-steroidal anti-inflammatory drugs (NSAIDs); disease-modifying anti-rheumatic drugs such as immunosuppressants; anti-TNF agents, such as infliximab, etanercept, and adalimumab; and anti B-cell therapies, such as rituximab.

Compounds used in the treatment of psychiatric diseases and disorders can be used in the methods of the invention. Such compounds include as $GABA_A$ modulators, such as benzodiazepines; $5HT_{1A}$ receptor agonists, such as buspirone; beta blockers; antipsychotics, such as dopamine receptor blockers and other drugs which modulate monoamine receptors, transporters or metabolism, such as tricyclic antidepressants, selective serotonin reuptake inhibitors, and monoamine oxidase inhibitors; lithium; and anti-epileptic drugs, such as those which block sodium channels, those which block T-type calcium channels, or those which block GABA transaminase or reuptake, including phenytoin, carbamazepine, valproate and vigabatrin. Compounds used in the treatment of a disease or disorder characterized by impairment of memory and/or loss of cognitive function can also be used in the methods of the invention, including, but not limited to such dopamine agonists and anticholinesterases.

VIII. Examples

Example 1. Synthesis of Compounds of the Invention

The syntheses of four analogs of ORG 27569, which were designed to test and evolve the computational model of the allosteric site of the $hCB_1$ receptor, are described. These are the 2-hydroxylated enantiomeric analogs (compound 1 and compound 2), the 2-cyclopropylphenyl analog (compound 3), and the 3-benzylindole analog (compound 4). The syntheses involve coupling a modified 4-(1-piperidino)phenethylamine with the previously reported 5-chloro-3-ethyl-1H-indole-2-carboxylic acid {Piscitelli, 2012} {Kotsikorou, 2013} or its similarly prepared 3-benzyl analog D7. Compound 1 and compound 2 enantiospecifically introduce hydroxyl groups during the synthesis as discussed below.

The synthesis of compound 1, shown in Scheme A/B, started with a kinetic resolution of racemic 2-(4-bromophenyl)oxirane A1 via ring opening with t-butylcarbamate A2 mediated via a chiral catalyst (R,R-salen) following the reported method. {Bartoli, 2004} This gave the chiral Boc protected (S)-aminoalcohol A3 in 42% yield and >99% enantiomeric excess (literature ee). The optical rotation (+46°) of the product matched that reported for the reported (S)-aminoalcohol A3. Similarly, treatment of A1 with (S,S-salen) provided the epimeric Boc protected (R)-aminoalcohol B3 that exhibited an optical rotation (−45°) supportive of the stereochemistry at the respective chiral carbons as S and R respectively. However, these literature assignments are based on analogous data and trends with past salen chemistry and not on a rigorous assignment (e.g. x-ray).

A second, independent, chiral synthesis of A3 was also examined via a chiral CBS-oxazaborolidine reduction {Corey, 1998} wherein reduction of ketones is precedented to give the S-stereochemistry product from the S-oxazaborolidine. Thus, reduction of 4'-bromo-2-chloroacetophenone (A7), followed by amination with ammonia gave the amino alcohol A8 which was converted to the Boc protected amine A3. The product A3 from this sequence afforded an optical rotation (+42°) close to that of the R,R-salen product A3 above, adding support to the stereochemical assignment.

Compound A8 from the CBS-oxazaborolidine reduction was catalytically reduced to remove the bromine and provide 2-hydroxy-2-phenethylamine. The optical rotation of the resulting product was measured and found to agree with authentic ((S)-2-hydroxy-2-phenethyl)amine from a commercial source. This confirmed the desired stereochemistry of A3 and by extension of B3.

The synthesis was continued by Ullman amination of A3 from the salen route with piperidine mediated with copper iodide, which provided A4 in 33% yield. Treatment of A4 with trifluoroacetic acid cleaved the Boc group to afford the (S)-aminoalcohol A5 in 100% yield. The corresponding (R)-aminoalcohol B5 was prepared in the same manner.

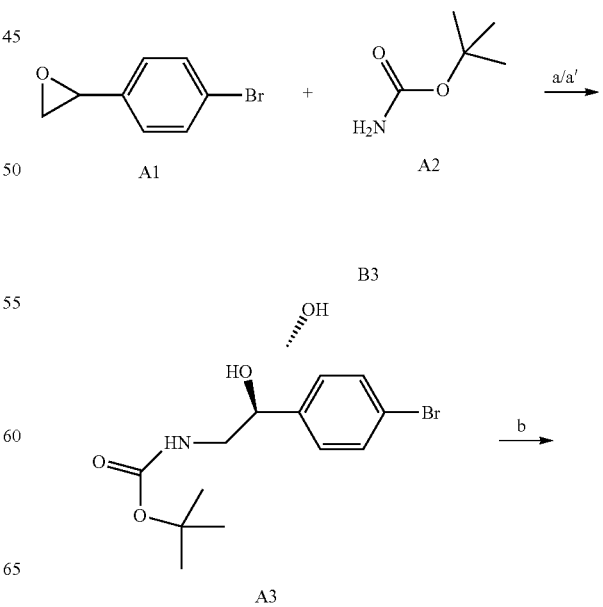

Scheme A/B

-continued

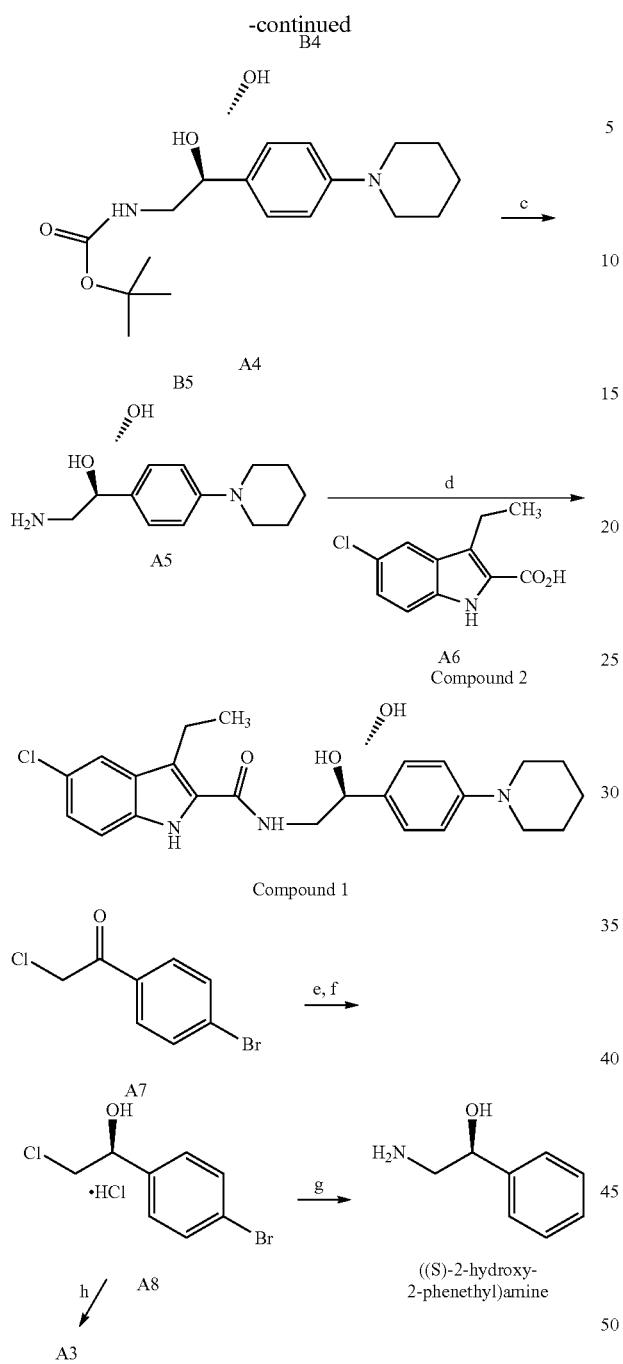

a. 4-nitrobenzoic acid. (R,R)-(-)-N,N'-Bis(3,5-di-tert-butyl-salicylidene-1,2-cyclohexanediaminocobalt II (A Series enantiomer), tert-BuOMe, RT, % Yield; b. L-proline, piperidine, CuI, DMSO, 90° C., 33%; c. TFA, CH₂Cl₂, RT; d. EDC, HOBt, Et₃N, DMF, 0° C. to RT, 12%; ??. (i) pTsOH hydrate, 1,3-dichloro-5,5-dimethylhydantoin, MeOH, 30-35° C., 7 h, (ii) HCl, THF, 60° C., 1.5 h, 100%; e. (S)-CBS-oxazaborolidine, BH₃, THF, RT, 1 h, 85%; f. NH₃, MeOH, RT, 5 d, 35%; g. (i) Na₂CO₃ (ii) H₂, Pd/C, EtOH, RT, 14 h, 48%; h. Boc₂O, Et₃N, MeOH, RT, 18 h, 89%.
a'. (S,S)-(-)N,N'-Bis(3,5-di-tert-butyl-salicylidene-1,2-cyclohexanediaminocobalt II was used for the B Series enantiomer.

The indole 2-carboxylic acid A6, prepared as referenced above, was coupled to each of the amines A5 and B5 to afford the corresponding amides compound 1 and compound 2, respectively, in 65% yield. The analogs were characterized for purity by HPLC and identity by ¹H NMR and high resolution mass spectrometry.

The 2-cyclopropylphenyl analog (compound 3) was prepared in five steps starting from commercially available 2-bromo-4-fluorobenzaldehyde C1 (Scheme C). Displacement of fluoride from C1 with piperidine at elevated temperature provided the desired N-aryl piperidine C2 in 96% yield.

Scheme C

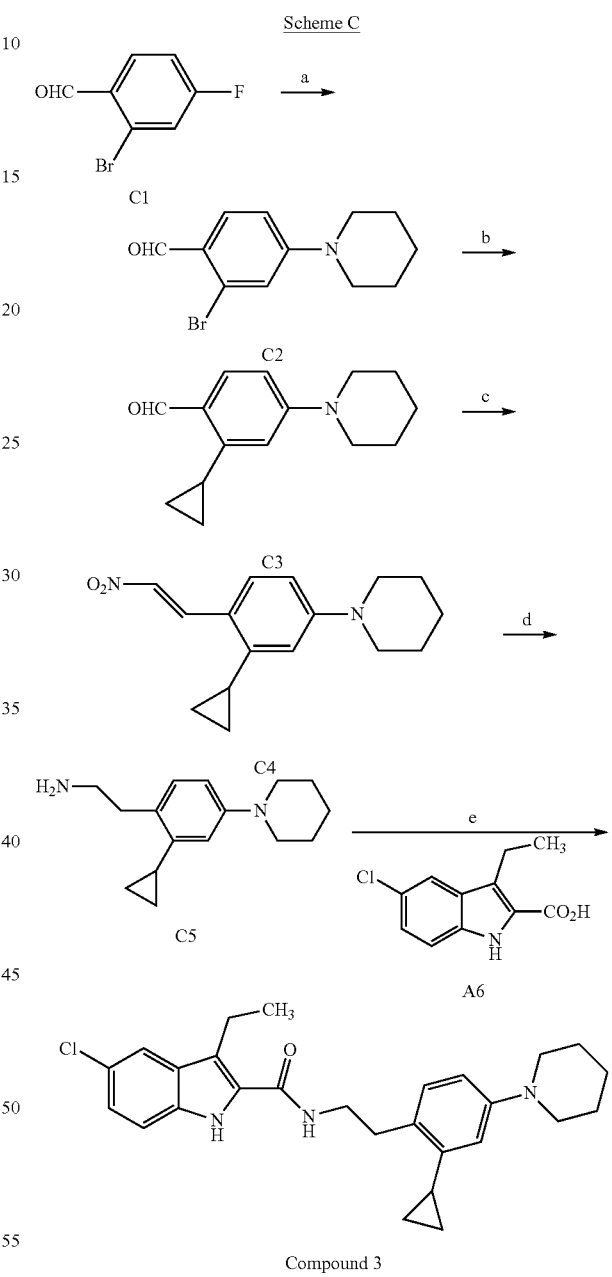

Compound 3 a. piperidine, K₂CO₃, DMF, 110° C., 96%; b. cyclpropylboronic acid, tricylcohexylphosphine, potassium phosphate monohydrate (tribasic), toluene, water, 100° C., 91%; c. NH₄OAc, nitromethane, 100° C., 62%, d. LAH, THF, RT to reflux, 73%, e. HOBt, EDC, DMF, Et₃N, 0° C. to RT, 44%.

Suzuki coupling between the aryl bromide C2 and cyclopropyl boronic acid gave the cyclopropyl substituted benzaldehyde C3 that was subjected to the Henry Reaction with nitromethane under dehydrating conditions to yield nitroalkene C4 in 63% yield. Reduction of C4 using lithium aluminum hydride provided the amine C5 in 73% yield. Coupling C5 and indole carboxylic acid A6 with a carbodiimide provided a 44% yield of the desired indole amide compound 3. Crystallization provided a sample of 99% purity (HPLC) for testing. High resolution mass spectrometry and $^1$H NMR spectroscopy supported the structural assignment.

Scheme D

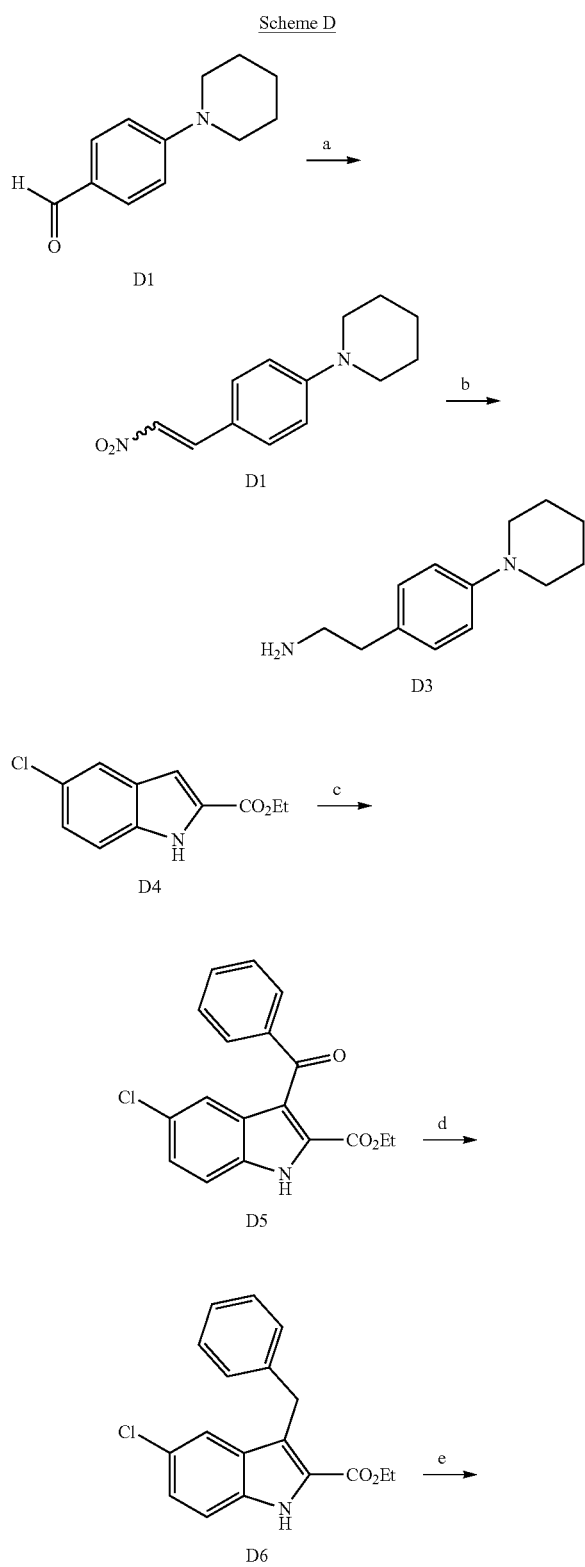

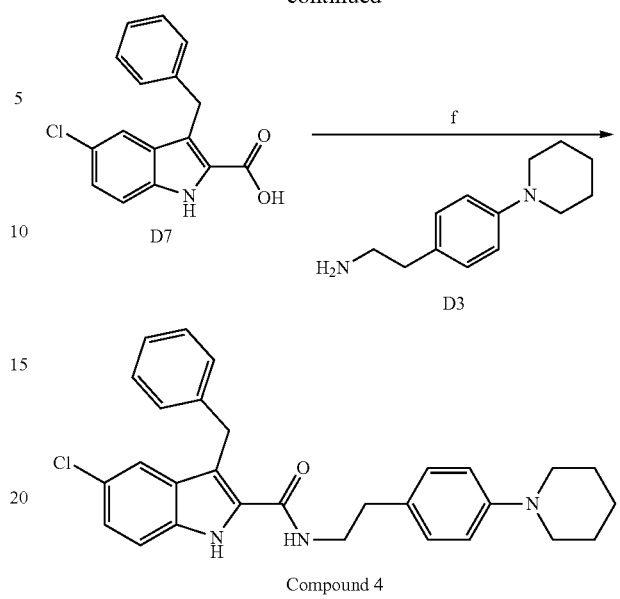

Compound 4 a) NH$_4$OAc, MeNO$_2$, 100° C., 3.5 h, b) LAH, THF, reflux, 1 h, c) benzoyl chloride, AlEt$_2$Cl, CH$_2$Cl$_2$, 0° C., 18 h, d) Et$_3$SiH, TFA, r.t, 3.5 h; e) NaOH, 1,4-dioxane, 120° C., 40 min; f) EDC, HOBt, DMF, 0° C. to r.t. 3 d.

The convergent synthesis of compound 4 couples amine D3 with indole acid D7 (Scheme D). Thus, commercially available 4-piperidinobenzaldhyde D1 was heated with nitromethane in a Henry Reaction to give a 53% yield of the nitroalkene D2. Reduction of D2 with lithium aluminum hydride provided the amine D3 in 83% yield. The 3-benzyl indole acid D7 was prepared from commercially available D4 in a manner similar to that reported above for the 3-ethyl indole acid A6. Thus, benzoylation of D4 with benzoyl chloride mediated by diethylaluminum chloride afforded D5 (31%). Reduction of the keto moiety to the methylene group was effected with triethylsilane in the presence of trifluoroacetic acid to provide D6 in 95% yield. Saponification of D6 gave D7 (98%). Coupling D7 and D3 with a carbodiimide gave the sought amide compound 4 (23%) after chromatography that afforded crystals from one of the product containing fractions. High resolution mass spectrometry and $^1$H NMR spectroscopy supported the structural assignment.

Scheme E

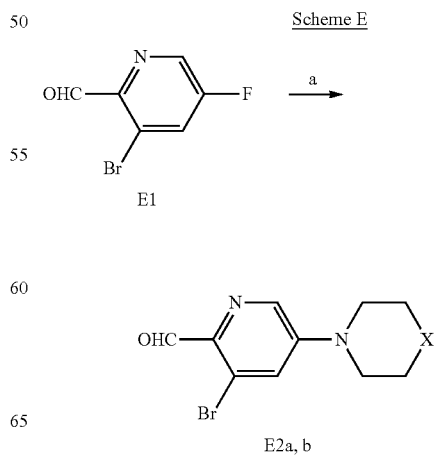

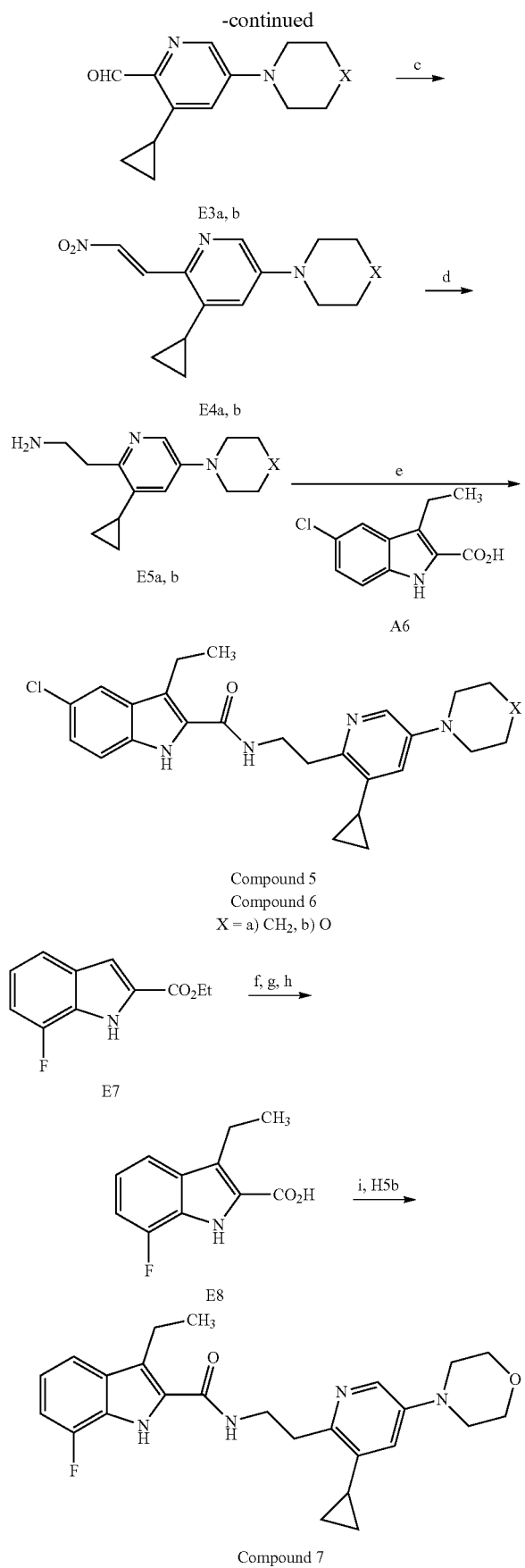

a) piperidine (X = CH$_2$) or morpholine (X = O), K$_2$CO$_3$, DMF, 110° C.;
b) cyclopropylboronic acid, tricylcohexylphosphine, potassium phosphate monohydrate (tribasic), toluene, water, 100° C.; c) NH$_4$OAc, nitromethane, 100° C.; d) LAH, THF, RT to reflux; e) HOBt, EDC, DMF, Et$_3$N, 0° C. to RT, 44%; f) 1. Et$_2$AlCl, THF, 0° C.; 2. AcCl, 0° C.-r.t.; g) Et$_3$SiH, TFA, r.t.; h) NaOH aq., 1,4-Dioxane, reflux; i) DCC, HOBt, CH$_2$Cl$_2$, r.t.

The syntheses of analogs of compound 3 involve coupling substituted pyridylethylamines (E5a, E5b) with 5-chloro-3-ethyl-1H-indole-2-carboxylic acid E6 or coupling E5b with 7-fluoro-3-ethyl-1H-indole-2-carboxylic acid E8 (Scheme H). Commercially available 3-bromo-5-fluoro-2-pyridinecarboxaldehyde E1 can be transformed to E5a,b first by displacement of fluoride with piperidine or morpholine in DMF to yield E2a,b. Suzuki coupling of the latter with cyclopropyl boronic acid can afford E3a,b. A Henry reaction with nitromethane under dehydrating conditions can provide nitroalkenes E4a,b. Subsequent reduction with lithium aluminum hydride gives E5a,b (73% in phenyl analog). The 5-chloroindole E6 is prepared as previously reported. The 7-fluoroindole E8 is similarly prepared from commercially available E7 by acylation with acetyl chloride, reduction with triethylsilane-trifluoroacetic acid, and hydrolysis with aqueous sodium hydroxide. Finally, coupling the acid A6/E8 with the appropriate E5 amine and suitable coupling reagents can be used to prepare the target compounds 5, 6, and 7.

Certain compounds of the invention are conformationally restrained through a furan ring linked to the amide moiety that can be synthesized following the route shown in Scheme F. Constructing the substituted furan amines F5a,b for coupling to the ORG indole acid A6 can be approached from various substituted furans or furan precursors according to known methods. For example, commercially available 3,4-dibromofuran F1 can be converted to the azido analog F2 by displacement of one of the bromides with sodium azide. Increased selectivity and reactivity can be obtained, if needed, by the known selective metal-halogen exchange of F1 with t-butyl lithium followed by trapping with an iodine source (steps a,b) followed by displacement with sodium azide, as demonstrated in excellent yield for trapping with a boron source (F2 where N$_3$ is B(OR)$_2$). The azido moiety (F2) is reduced with hydrogen sulfide to provide the corresponding amine F3. Suzuki coupling of F3 with the boronic acid (R=H) or borate esters F4a,b, commercially available as the N-phenyl-piperidine (X=CH$_2$) or -morpholine (X=O) analogs, provides the amino-furans F5a,b. Finally, condensation of F5a,b with previously described A6 will yield the target compounds 8 and 9. This route enables versatility in the syntheses of the target compounds by allowing for varied precursor furans (bromo, iodo, furanone), reaction sequences (condensation vs. coupling vs. displacement), and alternative coupling partners (boronate furan with piperidino phenyl iodide).

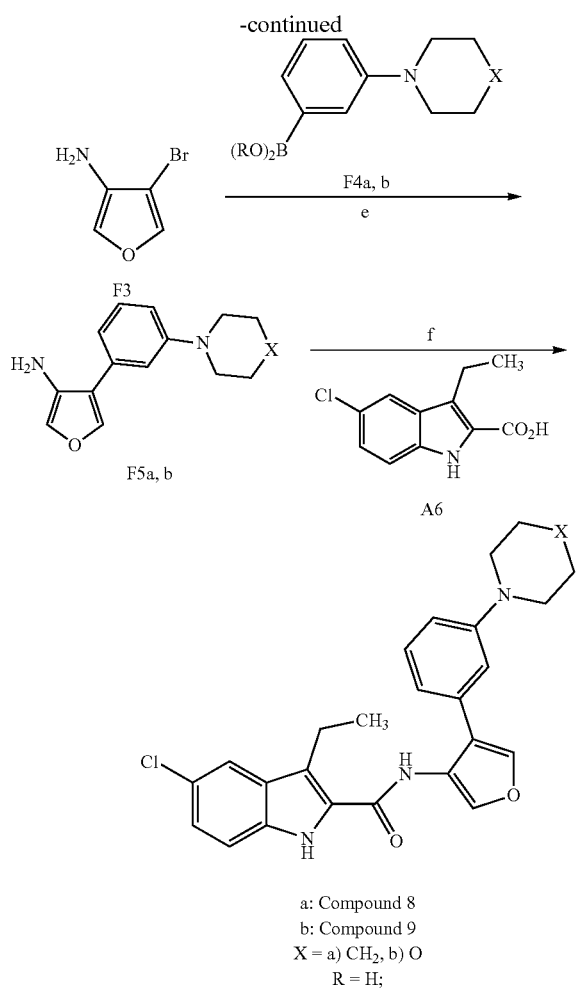

a: Compound 8
b: Compound 9
X = a) CH₂, b) O
R = H;
RR = tetramethylethyleneglycol ester a) t-BuLi; b) I₂; c) NaN₃; d) H₂S; e) PdCl₂(PPh₃)₂, Na₂CO₃; f) HOBt, EDC, DMF, Et₃N, 0° C. to RT;

Experimental

General:

Unless otherwise noted, all materials were obtained from commercial suppliers and used without further purification. Anhydrous solvents were obtained from Aldrich and used directly. All reactions involving air- or moisture-sensitive reagents were performed under a nitrogen atmosphere. Analytical thin-layer chromatography (TLC) was carried out on plates precoated with silica gel GHLF (250 μM thickness). TLC visualization was accomplished with a UV lamp. Silica gel chromatography was performed using RediSep pre-packed silica gel cartridges. HPLC analyses were performed using a Waters Emperor chromatography system comprised of a 1525 Binary Pump, 2487 Dual 1 Absorbance Detector, and a 717 plus Autosampler using a Waters C-18 reverse phase XBridge column (5 m; 4.6×100 mm; 254 nm; 1 mL/min). ¹H NMR spectra were run on a Bruker Advance 300 MHz NMR spectrometer. Low resolution mass spectra were run on a Perkin-Elmer Sciex API 150 EX mass spectrometer outfitted with APCI (atmospheric pressure chemical ionization) or ESI (turbospray) sources in positive or negative modes. High resolution mass spectrometry (HRMS) was performed using a Waters Synapt HDMS quadrupole time of flight (Q-TOF) mass spectrometer interfaced to a Waters Acquity UPLC system. HRMS data were acquired in negative electrospray MS resolution mode.

tert-Butyl N-[(2S)-2-(4-bromophenyl)-2-hydroxyethyl]carbamate (A3)

To a 20-dram vial was added a stir bar, 4-nitrobenzoic acid (0.228 g, 0.00135 mol), (R,R)-(−)-N,N'-Bis(3,5-di-tert-butylsalicylidene)-1,2-cyclohexanediaminocobalt(II) (0.510 g, 0.000844 mol) and methyl t-butyl ether (2.30 mL). The thick red solution was sonicated for 30 sec, capped (under air), then stirred at room temp until the thick solution became a dark brown color (about 20 min). t-Butyl carbamate (0.918 g, 0.00768 mol) and methyl t-butyl ether (0.77 mL) were then added. The contents of the vial were sonicated for 30 sec, then allowed to stir at room temp for 5 min. 2-(4-Bromophenyl)oxirane (3.50 g, 0.0169 mol) was then added in one portion. The contents of the vial were sonicated for 30 sec, capped (under air), then stirred at room temp for 60 h. At this point the reaction was determined to be complete by TLC [MK6F SiO₂, 9:1 CH₂Cl₂:EtOAc, phosphomolybdic acid (PMA) stain visualization]. The system was evaporated in vacuo until a residue remained. The material was chromatographed on an ISCO Automated Chromatograph [220 g column; 0-10% linear gradient EtOAc in CH₂Cl₂; crude dissolved in 100% CH₂Cl₂]. The product-containing fractions were evaporated in vacuo, azeotropically evaporated with CH₂Cl₂ (3×50 mL) and high-vacuum dried to yield a tan solid (1.03 g, 42%, 13508-17-41). The NMR data obtained matched the published data. ¹H NMR (300 MHz; CDCl₃): δ 7.45-7.50 (m, 2H), 7.23-7.27 (m, 2H), 4.90 (bs, 1H), 4.76-4.84 (m, 1H), 3.40-3.50 (m, 1H), 3.28 (bs, 1H), 3.16-3.26 (m, 1H), 1.45 (s, 9H).

tert-Butyl N-[(2S)-2-hydroxy-2-[4-(piperidin-1-yl)phenyl]ethyl]carbamate (A4)

To a glass vial was added tert-butyl N-[(2S)-2-(4-bromophenyl)-2-hydroxyethyl]carbamate (30 mg, 0.95 mmol), CuI (28 mg, 0.147 mmol, 15.5 mol %), L-proline (29 mg, 0.25 mmol, 26.5 mol %), potassium carbonate (326 mg, 2.36 mmol, 2.5 eq), and anhydrous DMSO (2.5 mL). The vial was flushed with nitrogen and piperidine (0.36 mL, 3.6 mmol, 3.8 eq) was added. The vial was sealed with a cap that was equipped with a pressure-release safety septum and the stirred reaction mixture was heated at 90° C. for four days. The reaction mixture was allowed to cool at room temperature and partitioned between water and EtOAc. The layers were separated and the aqueous phase was extracted with EtOAc. The organic extracts were combined, washed with brine, dried (MgSO₄), filtered, and the filtrate was concentrated to give 0.34 g of the crude product as an oil. The crude product was combined with 0.11 g of crude product obtained from an earlier run of the reaction wherein tert-butyl N-[(2S)-2-(4-bromophenyl)-2-hydroxyethyl]carbamate (100 mg, 0.32 mmol), CuI (8.4 mg, 0.044 mmol, 13.8 mol %), L-proline (8.5 mg, 0.074 mmol, 23.0 mol %), potassium carbonate (97 mg, 0.70 mmol, 2.2 eq), anhydrous DMSO (0.67 mL) and piperidine (0.090 mL, 0.91 mmol, 2.8 eq) were employed. The crude product was purified by flash chromatography over SiO₂ (24 g) with a Hex:EtOAc gradient (100:0 to 40:60) to give 135 mg (33%) of the desired product as a pale peach solid. ¹H NMR (300 MHz; CDCl₃): δ 7.23 (d, J=8.7 Hz, 2H), 6.91 (d, J=8.7 Hz, 2H), 4.90 (br s, 1H), 4.73 (m, 1H), 3.43 (m, 1H), 3.25 (m, 1), 3.15 (m, 4H), 2.65 (br s, 1H), 1.70 (m, 4H), 1.57 (m, 2H), 1.45 (s, 9H).

(1S)-2-Amino-1-[4-(piperidin-1-yl)phenyl]ethan-1-ol (A5)

To a stirred solution of tert-butyl N-[(2S)-2-hydroxy-2-[4-(piperidin-1-yl)phenyl]ethyl]carbamate (126 mg, 0.39 mmol) in $CH_2Cl_2$ (2 mL) was added dropwise trifluoroacetic acid (0.80 mL) under nitrogen at room temperature. After 1 h the reaction mixture was concentrated and the crude product was partitioned between 15% NaOH and $CH_2Cl_2$. The layers were separated and the aqueous phase was extracted with $CH_2Cl_2$. The organic extracts were combined, washed with brine, dried ($MgSO_4$), filtered, and concentrated to give 119 mg (>100%) of the crude product as a tan amorphous solid. The crude product was used directly without further purification. $^1H$ NMR (300 MHz; DMSO-$d_6$): δ 7.14 (d, J=8.6 Hz, 2H), 6.87 (d, J=8.6 Hz, 2H), 5.14 (br s, 1H), 4.36 (br s, 1H), 3.08 (m, 4H), 2.63 (m, 2H), 1.60 (m, 4H), 1.53 (m, 2H). ES MS 221 (M+H)$^+$, 203 (M+H—$H_2O$)$^+$.

5-Chloro-3-ethyl-N-[(2S)-2-hydroxy-2-[4-(piperidin-1-yl)phenyl]ethyl]-1H-indole-2-carboxamide (Compound 1)

Crude (1S)-2-amino-1-[4-(piperidin-1-yl)phenyl]ethan-1-ol (0.39 mmol), 5-chloro-3-ethyl-1H-indole-2-carboxylic acid (90 mg, 0.40 mmol, 1 eq), 1-hydroxybenzotriazole hydrate (min 20% $H_2O$) (96 mg, 0.57 mmol, 1.5 eq), triethylamine (0.16 mL, 1.15 mmol, 2.9 eq) and DMF (4 mL) were combined and the solution was cooled in an ice-water bath under nitrogen. To the stirred cold solution was added 1-ethyl-(3-dimethylamino)propyl)carbodiimide hydrochloride (120 mg, 0.70 mmol, 1.8 eq) followed by DMF (2 mL) and the reaction mixture was allowed to warm to room temperature. After 4 d the solvent was removed in vacuo and the crude product was partitioned between saturated $NaHCO_3$ and EtOAc. The organic phase was separated, dried ($MgSO_4$), filtered, and concentrated to give a red solid (340 mg). Dichloromethane was added to the solid and the suspension was filtered. The filtered red solid (85 mg) was set aside and the filtrate was purified by flash chromatography over $SiO_2$ (12 g), with a Hex:EtOAc gradient (100:0 to 30:70) to give an off-white solid which was dried at 70° C. under high vacuum to give 20.5 mg (12%) of pure desired product. Additional product was obtained by extraction of the above aqueous solution with EtOAc, adding the less pure fractions of the above flash column as well as the filtered red solid described above to give 92 mg of product that was 89% pure according to HPLC [HPLC Conditions: XBridge C-18 reverse phase column; 5 m; 4.6×100 mm; 254 nm; 1 mL/min; $CH_3CN:H_2O$ with 0.05% TFA (60:40).] $^1H$ NMR (500 MHz, DMSO-$d_6$, 60° C.): δ 11.29 (br s, 1H), 7.63 (m, 2H), 7.39 (d, J=8.5 Hz, 1H), 7.22 (d, J=9.0 Hz, 2H), 7.17 (dd, J=2.3 Hz, 8.8 Hz, 1H), 6.88 (d, J=8.5 Hz, 2H), 4.67 (dd, J=4.8 Hz, 7.8 Hz, 1H), 3.57 (dm, J=13.0 Hz, 1H), 3.36 (ddd, J=4.5 Hz, 7.5 Hz, 13.0 Hz, 1H), 3.11 (m, 4H), 2.96 (q, J=7.5 Hz, 2H), 1.61 (m, 4H), 1.53 (m, 2H), 1.14 (t, J=7.5 Hz, 3H). HRMS ES+ Calc. m/z for $C_{24}H_{29}ClN_3O_2$: 426.1943. Observed: 426.1941.

5-Chloro-3-ethyl-N-[(2R)-2-hydroxy-2-[4-(piperidin-1-yl)phenyl]ethyl]-1H-indole-2-carboxamide (Compound 2)

The title compound was prepared as described for compound 1 except for using the enantiomeric catalyst (R,R)-(−)-N,N'-Bis(3,5-di-tert-butylsalicylidene)-1,2-cyclohexanediaminocobalt(II). The material was 98.3% pure by HPLC [HPLC Conditions: XBridge C-18 reverse phase column; 5 μm; 4.6×100 mm; 254 nm; 1 mL/min; $CH_3CN:H_2O$ with 0.05% TFA (40:60).] $^1H$ NMR (300 MHz; DMSO-$d_6$): δ 11.42 (s, 1H), 7.83 (m, 1H), 7.66 (m, 1H), 7.40 (d, J=8.7 Hz, 1H), 7.22 (d, J=8.7 Hz, 2H), 7.18 (m, 1H), 6.90 (d, J=8.7 Hz, 2H), 5.41 (d, J=4.1 Hz, 1H), 4.66 (m, 1H), 3.56 (m, 1H), 3.30 (m, 1H), 3.10 (m, 4H), 2.97 (q, J=7.5 Hz, 2H), 1.61 (m, 4H), 1.53 (m, 2H), 1.12 (t, J=7.5 Hz, 3H). ES+ MS Calcd: 426.19 (M+H)$^+$; Found: 426.3. ES− MS Calcd: 424.19 (M−H)$^+$; Found: 424.5. HRMS ES+ Calc. m/z for $C_{24}H_{29}ClN_3O_2$: 426.1943. Observed: 426.19.

2-Bromo-4-(piperidin-1-yl)benzaldehyde (C2)

2-Bromo-4-fluorobenzaldehyde (2.0 g, 0.0099 mol), piperidine (1.03 mL, 0.0104 mol, 1.05 eq), potassium carbonate (1.57 g, 0.0114 mol, 1.15 eq) and anhydrous DMF (20 mL) were combined and the stirred reaction mixture was heated at 110° C. under nitrogen for 18 h. The reaction mixture was allowed to cool at room temperature, concentrated, and partitioned between water and EtOAc. The organic phase was separated, washed with brine, dried ($MgSO_4$), filtered, and concentrated. The crude product was purified by flash chromatography over $SiO_2$ (40 g) with a hexane:EtOAc gradient (100:0 to 60:40) to give 2.55 g (96%) of the title compound as a yellow oil. $^1H$ NMR (300 MHz, $CDCl_3$): δ 10.07 (s, 1H), 7.78 (d, J=8.9 Hz, 1H), 6.96 (d, J=2.0 Hz, 1H), 6.80 (d, J=8.8 Hz, 1H), 3.40 (s, 4H), 1.68 (s, 6H).

2-Cyclopropyl-4-(piperidin-1-yl)benzaldehyde (C3)

2-Bromo-4-(piperidin-1-yl)benzaldehyde (1.46 g) 0.00544 mol), cyclopropylboronic acid (0.732 g, 0.00852 mol, 1.56 eq), tricyclohexylphosphine (0.172 g, 0.00061 mol, 11.2 mol %), potassium phosphate monohydrate (tribasic) (2.5 g, 0.0109 mol, 2 eq), toluene (23 mL) and water (0.20 mL, 0.0111 mmol, 2 eq) were combined and the stirred mixture was heated at 100° C. under nitrogen. Palladium acetate (0.077 g, 0.34 mmol, 6.3 mol %) was added to the reaction mixture and heating was continued for 5 h. The reaction mixture was allowed to stand overnight at room temperature, filtered through a pad of celite, and the pad was washed with EtOAc. The filtrate was concentrated and the crude product was purified by flash chromatography over $SiO_2$ (40 g) with a hexane:EtOAc gradient (100:0 to 60:40) to give 1.14 g (91%) of the desired product as a yellow oil. $^1H$ NMR (300 MHz, $CDCl_3$): δ 10.32 (s, 1H), 7.71 (d, J=8.7 Hz, 1H), 6.73 (d, J=8.6 Hz, 1H), 6.51 (s, 1H), 3.37 (s, 4H), 2.60 (m, 1H), 1.66 (s, 6H), 1.02 (m, 2H), 0.74 (m, 2H).

1-{3-Cyclopropyl-4-[(E)-2-nitroethenyl]phenyl}piperidine (C4)

2-Cyclopropyl-4-(piperidin-1-yl)benzaldehyde (1.1 g, 0.0048 mol), ammonium acetate (0.785 g, 0.0102 mol, 2.1 eq) and nitromethane (12 mL) were combined in a round bottom flask and the reaction mixture was heated at 100° C. under nitrogen for 4 h. The reaction mixture was allowed to cool at room temperature, concentrated, and partitioned between saturated $NaHCO_3$ and EtOAc. The organic phase was separated, washed with brine, dried ($MgSO_4$), filtered, and concentrated. The crude product was purified by flash chromatography over $SiO_2$ (40 g) with a hexane:EtOAc gradient (100:0 to 70:30) to give 0.81 g (62%) of the desired product as a dark red-brown solid. $^1H$ NMR (300 MHz, CDCl$_3$): δ 8.60 (d, J=13.4 Hz, 1H), 7.55 (d, J=13.4 Hz, 1H), 7.44 (d, J=8.8 Hz, 1H), 6.71 (dd, J=2.6 Hz, 8.9 Hz, 1H), 6.64 (d, J=2.5 Hz, 1H), 3.34 (m, 4H), 2.04 (m, 1H), 1.66 (s, 6H), 1.05 (m, 2H), 0.71 (m, 2H).

2-[2-Cyclopropyl-4-(piperidin-1-yl)phenyl]ethan-1-amine (C5)

To a stirred solution of 1-{3-cyclopropyl-4-[(E)-2-nitroethenyl]phenyl}piperidine (810 mg, 3 mmol) in anhydrous THF (50 mL) was added dropwise lithium aluminum hydride (1 N in THF) (16 mL, 16 mmol, 5.3 eq) at room temperature under nitrogen. The reaction mixture was heated at reflux for 1 h. The reaction mixture was allowed to cool at room temperature and then cooled in an ice-water bath. To the stirred cold turbid mixture was added dropwise water (0.6 mL), followed by 15% NaOH (0.6 mL) and finally water (1.8 mL). The quenched mixture was filtered through a pad of celite and the pad was washed with EtOAc. The filtrate was washed with saturated NaHCO$_3$ followed by brine, dried (MgSO$_4$), filtered, and the filtrate was concentrated to give 0.534 g (73%) of the desired product as a yellow oil. $^1$H NMR indicates one or more impurities are present. The compound was used directly without further purification. $^1$H NMR (300 MHz, CDCl$_3$): δ 7.03 (d, J=8.2 Hz, 1H), 6.71 (dd, J=2.7 Hz, 8.3 Hz, 1H), 6.58 (d, J=2.6 Hz, 1H), 3.08 (m, 4H), 2.95 (m, 2H), 1.98 (m, 5), 1.69 (m, 4H), 1.56 (m, 2H), 0.92 (m, 2H), 0.65 (m, 2H).

5-Chloro-N-{2-[2-cyclopropyl-4-(piperidin-1-yl)phenyl]ethyl}-3-ethyl-1H-indole-2-carboxamide (Compound 3)

To an ice-water cooled stirred mixture of 5-chloro-3-ethyl-1H-indole-2-carboxylic acid (73 mg, 0.326 mmol), 1-hydroxybenzotriazole (61 mg, 0.45 mmol, 1.38 eq), triethylamine (0.12 mL, 0.86 mmol, 2.6 eq) and DMF (3 mL) was added 1-ethyl-(3-(3-dimethylamino)propyl)-carbodiimide hydrochloride (78 mg, 0.41 mmol, 1.25 eq) followed by DMF (1 mL). The reaction mixture was stirred at room temperature overnight. After 24 h, the reaction mixture was concentrated and partitioned between water and EtOAc. The organic phase was separated, washed with brine, dried (MgSO$_4$), filtered, and concentrated. The crude product was partially purified by flash chromatography over SiO$_2$ (12 g) with a hexane:EtOAc gradient (100:0 to 60:40) to give 67 mg of a pale tan solid. The solid was dissolved in EtOAc and the solution was partially concentrated in vacuo. The suspension was filtered and the filtered solid was washed with Et$_2$O and dried to give 27 mg (18%) of the desired product as a white solid. The filtrate was concentrated and dried to give 39 mg of slightly impure product as a pale tan solid. HPLC analysis of the white solid indicates the product is 99% pure. [HPLC Conditions: Waters XBridge C-18 reverse phase column; 5 mm; 4.6×100 mm; 254 nm; 1 mL/min; CH$_3$CN:H$_2$O with 0.05% TFA (80:20)]. $^1$H NMR (300 MHz, CDCl$_3$): δ 11.34 (br s, 1H), 8.03 (br t, J=5.6 Hz, 1H), 7.66 (d, J=1.9 Hz, 1H), 7.40 (d, J=8.7 Hz, 1H), 7.18 (dd, J=2.0 Hz, 8.7 Hz, 1H), 7.01 (d, J=8.4 Hz, 1H), 6.68 (dd, J=2.5 Hz, 8.3 Hz, 1H), 6.45 (d, J=2.4 Hz, 1H), 3.49 (m, 2H), 3.03 (m, 4H), 2.95 (m, 4H), 2.04 (m, 1H), 1.59 (m, 4H), 1.51 (m, 2H), 1.14 (t, J=7.4 Hz, 3H), 0.90 (m, 2H), 0.65 (m, 2H). ES+ HRMS Calcd: 450.2307 (M+H)$^+$; Found: 450.2310.

1-[4-(2-Nitroethenyl)phenyl]piperidine (D2)

To a 250-mL round-bottomed flask containing a stir bar was added 4-piperidin-1-yl-benzaldehyde (4.90 g, 0.0259 mol), ammonium acetate (3.66 g, 0.0461 mol), and nitromethane (51.0 mL). The system was fitted with a reflux condenser, placed under a N$_2$ atmosphere and heated to reflux for 3.5 h. At this point the system was cooled to room temperature and evaporated in vacuo until a residue remained. The red-brown solid was dissolved in ethyl acetate (250 mL) and 1 N HCl (200 mL). The layers were separated, re-extracting the aqueous layer with ethyl acetate (3×200 mL). The organic layers were combined and then washed with a saturated solution of sodium bicarbonate (200 mL). The aqueous layer was back-extracted once with ethyl acetate (200 mL). The organic layers were combined, dried over sodium sulfate, filtered, evaporated in vacuo, and high-vacuum dried to yield a bright red solid. The crude product was chromatographed via ISCO Automated Chromatography [220 g column; 0-25% linear gradient EtOAc in hexanes, then isocratic 25% EtOAc in hexanes; crude dissolved in 100% CHCl$_3$]. The desired fractions were evaporated in vacuo and high-vacuum dried to yield a bright red solid (3.16 g, 53%).

2-[4-(Piperidin-1-yl)phenyl]ethan-1-amine (D3)

To a 500-mL round-bottomed flask containing 1-[4-(2-nitroethenyl)phenyl]piperidine (1.50 g, 0.00646 mol), which had been high-vacuum dried overnight, was added a stir bar and anhydrous THF (91.2 mL). The system was placed under a N$_2$ atmosphere. Lithium aluminum hydride (30.4 mL of a 1 M solution in THF, 0.0304 mol) was added dropwise at room temperature over 2 min. The system was fitted with a reflux condenser, placed under a N$_2$ atmosphere and heated to reflux for 1 h. At this point the system was cooled to room temperature. The system was cooled to 0° C. and water (1.15 mL) was added dropwise with vigorous stirring. A 15% solution of NaOH (1.15 mL) was added followed by more water (3.46 mL). A white precipitate was formed which was filtered away via a pad of Celite, washing with ethyl acetate. The clear yellow filtrate was evaporated to a total volume of 60 mL. A saturated solution of sodium bicarbonate (80 mL) was added and the layers separated, re-extracting the aqueous layer with ethyl acetate (2×50 mL). The organic layers were combined and washed with brine (200 mL). The aqueous layer was re-extracted with ethyl acetate (2×60 mL). The organic layers were combined, dried over sodium sulfate, filtered, evaporated in vacuo, azeotroped with CH$_2$Cl$_2$ (3×100 mL) and high-vacuum dried to yield an orange oil (1.11 g, 83%).

Ethyl 3-benzoyl-5-chloro-1H-indole-2-carboxylate (D5)

A 500-mL round-bottomed flask containing a stir bar was heat-dried under a stream of N$_2$ using a heat gun. Ethyl-5-chloroindole-2-carboxylate (1.70 g, 0.00760 mol) and anhydrous dichloromethane (40.0 mL) were added and the system cooled to 0° C. Diethylaluminum chloride (15.0 mL of a 1 M solution in heptanes, 0.0150 mol) was then added dropwise over 5 min. The system was stirred at 0° C. for 45 min, then a solution of benzoyl chloride (2.14 g, 0.0152 mol) in anhydrous dichloromethane (40.0 mL) was added dropwise over 5 min. The system was allowed to warm to room temp overnight. At this point the system was cooled to 0° C. With vigorous stirring, a saturated solution of sodium bicarbonate (100 mL) was added slowly. Dichloromethane (100 mL) and brine (100 mL) were added in an unsuccessful attempt to break up the resulting emulsion. The mixture was filtered over a pad of Celite, washing with dichloromethane.

The resulting biphasic filtrate was evaporated in vacuo to remove some of the solvent. The layers were separated, re-extracting the aqueous layer with $CH_2Cl_2$ (300 mL). The organic layers were combined and washed with brine (200 mL). The aqueous layer was re-extracted with $CH_2Cl_2$ (200 mL). The organic layers were combined, dried over sodium sulfate, filtered, evaporated in vacuo, and high-vacuum dried. The crude material (3.00 g) was chromatographed on an ISCO Automated Chromatograph [120 g column; 0-50% linear gradient EtOAc in hexanes; crude dissolved in 100% $CH_2Cl_2$]. The desired fractions were evaporated in vacuo, azeotroped once with $CH_2Cl_2$ (50 mL), and high-vacuum dried to yield a light yellow solid (0.780 g, 31%).

Ethyl 3-benzyl-5-chloro-1H-indole-2-carboxylate (D6)

To a 20-dram vial containing a stir bar was added ethyl 3-benzoyl-5-chloro-1H-indole-2-carboxylate (0.450 g, 0.00137 mol) and TFA (5.4 mL). The system was fitted with a septum cap and placed under a $N_2$ atmosphere. Triethylsilane (0.639 g, 0.00549 mol) was added dropwise over 30 sec. The resulting dark yellow solution was then stirred under $N_2$ at room temp. After 30 min the system was a mustard-yellow slurry. After stirring for a total of 3.5 h the layers were separated and the aqueous layer was extracted with ethyl acetate (60 mL). The organic layers were combined and washed with brine (75 mL). The aqueous layer was re-extracted with ethyl acetate (60 mL). The organic layers were combined, dried over sodium sulfate, filtered, evaporated in vacuo, and high-vacuum dried to yield an off-white solid (0.410 g, 95%).

3-Benzyl-5-chloro-1H-indole-2-carboxylic acid (D7)

To a 100-mL round-bottomed flask containing a stir bar was added ethyl 3-benzyl-5-chloro-1H-indole-2-carboxylate (0.380 g, 0.00121 mol) and 1,4-dioxane (9.0 mL). Sodium hydroxide (6.06 mL of a 1 N solution, 0.00606 mol) was then added in one portion. The system was fitted with a reflux condenser and heated at reflux temperature under an atmosphere of $N_2$ for 40 min. At this point the system was cooled to room temperature. Aqueous HCl (30 mL of a 1 N solution) was added slowly to quench. The resulting suspension was stirred at room temperature for 5 min. Ethyl acetate (40 mL) was added to dissolve the solid. The layers were separated, re-extracting the aqueous layer with ethyl acetate (2×40 mL). The organic layers were combined, dried over sodium sulfate, filtered, evaporated in vacuo, and high-vacuum dried to yield the product as a peach-colored solid (0.339 g, 98%).

3-Benzyl-5-chloro-N-{2-[4-(piperidin-1-yl)phenyl]ethyl}-1H-indole-2-carboxamide (Compound 4)

To a 20-dram vial containing a stir bar was added 2-[4-(piperidin-1-yl)phenyl]ethan-1-amine (0.138 g, 0.000676 mol), 3-benzyl-5-chloro-1H-indole-2-carboxylic acid (0.165 g, 0.000577 mol), and DMF (5.3 mL). 1-Hydroxybenzotriazole hydrate (0.139 g of a 20% water by weight solid, 0.000797 mol) was then added in one portion. The system was placed under an atmosphere of $N_2$ and then triethylamine (0.152 g, 0.00150 mol) was added dropwise over 1 min. The resulting solution was cooled to 0° C. A slurry of N-(3-dimethylaminopropyl)-N'-ethylcarbodiimide hydrochloride (0.138 g, 0.000722 mol) in N,N-dimethylformamide (1.8 mL) was then added in one portion. The resulting suspension was warmed to room temp, where it became an orange-colored solution. The system was allowed to stir at room temperature for 3 days. At this point the contents of the vial were transferred to a 100 mL round-bottomed flask with ethyl acetate and evaporated in vacuo until a residue remained. The residue was partitioned between ethyl acetate (50 mL) and brine (50 mL). The layers were separated, re-extracting the aqueous layer with ethyl acetate (3×50 mL). The organic layers were combined, dried over sodium sulfate, filtered, evaporated in vacuo, and high-vacuum dried. The crude material (0.463 g) was chromatographed on an ISCO Automated Chromatograph [24 g column; 0-50% linear gradient EtOAc in hexanes, then isocratic 100% EtOAc; crude dissolved in 100% $CH_2Cl_2$]. One fraction yielded white needles upon standing. This fraction was filtered, washed with hexanes, and high-vacuum dried to yield a white solid (0.022 g, 8%). Further product from other fractions was also obtained (0.042 g, 15%), bringing the total yield for this step to 23%. The crystalline material was 98.6% pure by HPLC [HPLC Conditions: XBridge C-18 reverse phase column; 5 μm; 4.6×100 mm; 254 nm; 1 mL/min; $CH_3CN:H_2O$ with 0.05% TFA (70:30).] $^1H$ NMR (300 MHz; $CDCl_3$): δ 9.23 (br s, 1H), 7.55 (d, J=1.9 Hz, 1H), 7.36 (d, J=8.6 Hz, 1H), 7.23 (m, 5H), 6.99 (m, 2H), 6.93 (m, 2H), 6.87 (m, 1H), 5.83 (m, 1H), 4.12 (s, 2H), 3.54 (m, 2H), 3.12 (m, 4H), 2.64 (t, J=6.8 Hz, 2H), 1.72 (m, 4H), 1.56 (m, 2H). ES+ MS Calcd: 472.21 $(M+H)^+$; Found: 472.7. ES− MS Calcd: 470.21 $(M−H)^+$; Found: 470.7.

Compounds were tested using a GTPγS assay as previously described (Shore D M, et al. *J Biol Chem.* 2014; 289(9):5828-45; incorporated herein by reference in its entirety). Compounds were tested using an ERK assay as previously described (Kapur A, et al. *J Biol Chem.* 2009; 284:29817-29827; incorporated herein by reference in its entirety).

Figures 3, 4:
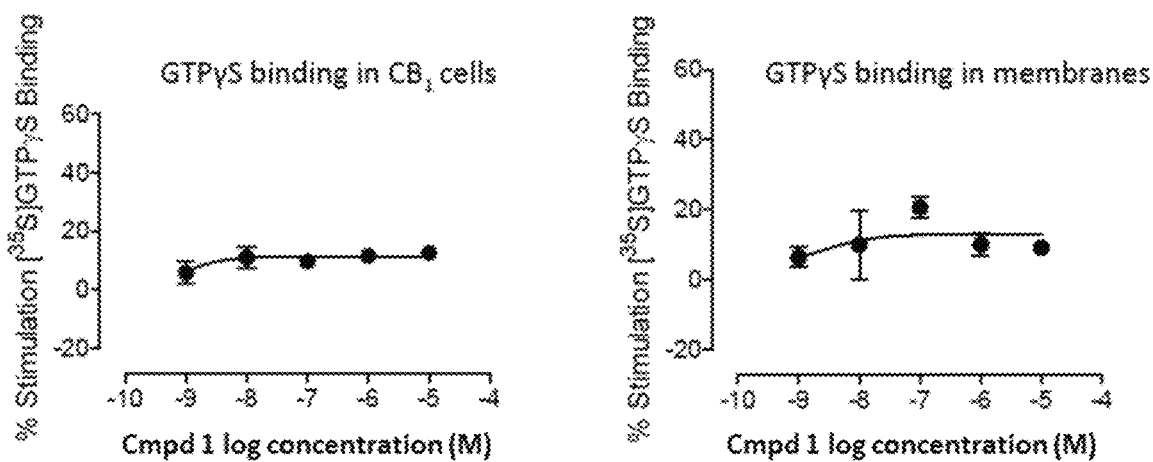
FIG. 3 shows the effects of the compounds of the invention on binding and G protein-mediated signaling. Compound 1 is a less potent and efficacious negative allosteric modulator of $CB_1$ than ORG27569. Compound 2 is a more potent negative allosteric modulator than ORG27569 and compound 3 is not an allosteric modulator of $CB_1$.
FIG. 4 shows the effect of compound 1 on basal G protein signaling.

FIG. 3 shows the effects of the compounds of the invention on binding and G protein-mediated signaling. Compound 1 is a less potent and efficacious negative allosteric modulator of $CB_1$ than ORG27569. Compound 2 is a more potent negative allosteric modulator than ORG27569 and compound 3 is not an allosteric modulator of $CB_1$.

FIG. 4 shows the effect of compound 1 on basal G protein signaling. Compound 1 has no effect on GTP-gamma-S binding.

Figure 5:
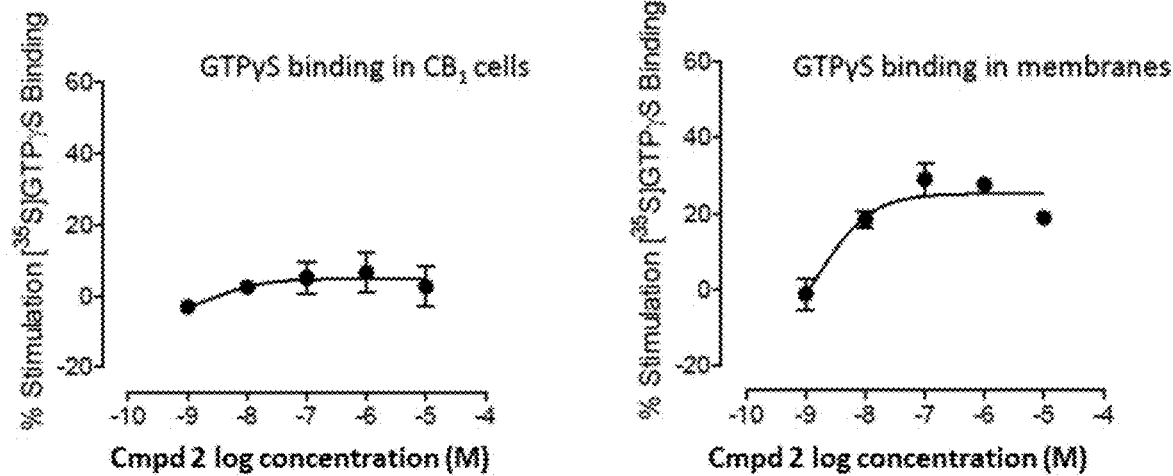
FIG. 5 shows the effect of compound 2 on basal G protein signaling.

FIG. 5 shows the effect of Compound 2 on basal G protein signaling. Compound 2 is a partial agonist in membranes.

Figure 6:
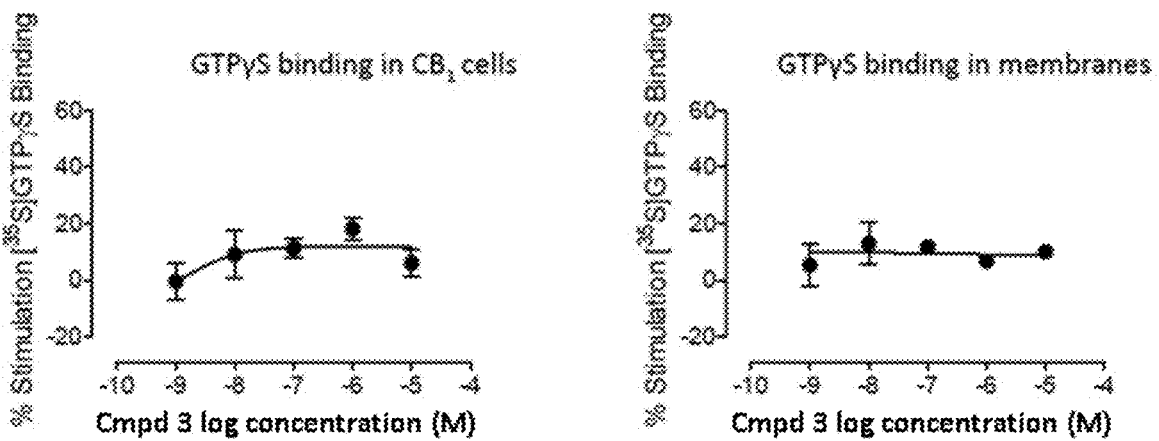
FIG. 6 shows the effect of compound 3 on basal G protein signaling.
Figure 7:
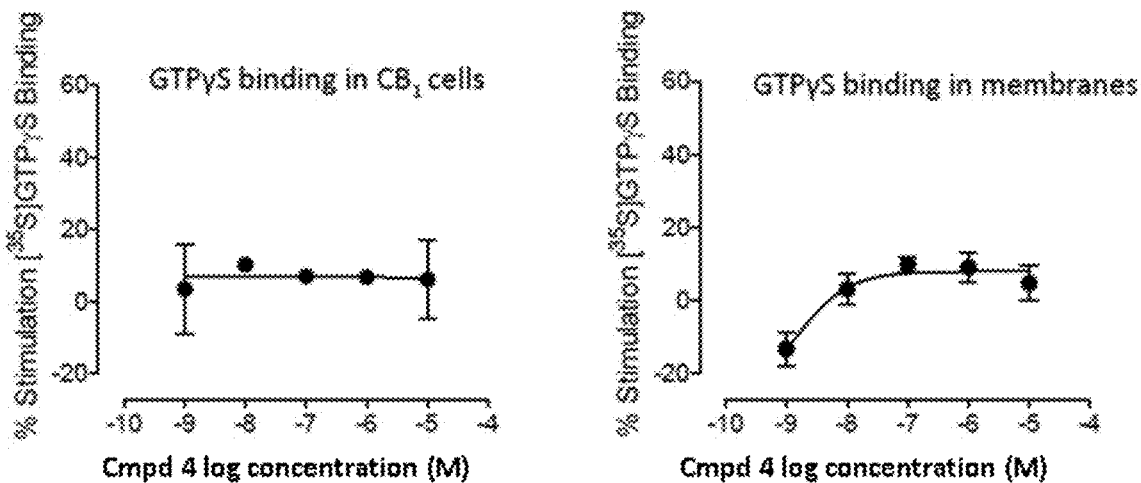
FIG. 7 shows the effect of compound 4 on basal G protein signaling.

FIG. 6 and FIG. 7 show the effect of compounds 3 and 4 on basal G protein signaling. Compound 3 and 4 have no effect on GTP-gamma-S binding.

Figure 8:
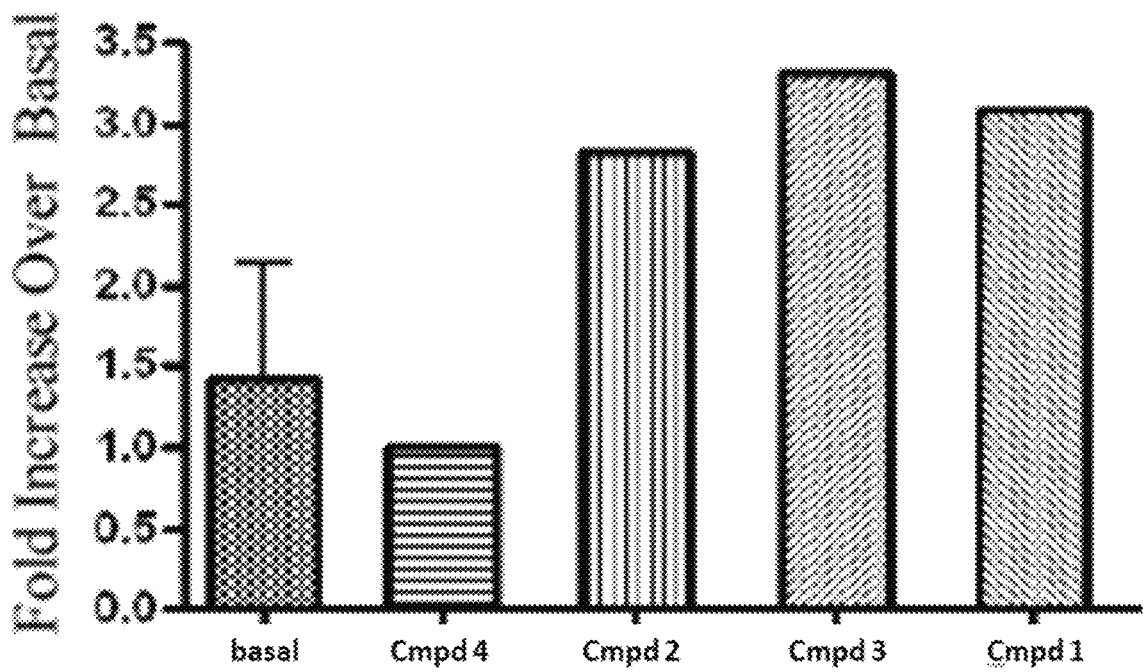
FIG. 8 shows the effects of the compounds of the invention on ERK signaling.

FIG. 8 shows the effects of the compounds of the invention on ERK signaling.

Figure 9:
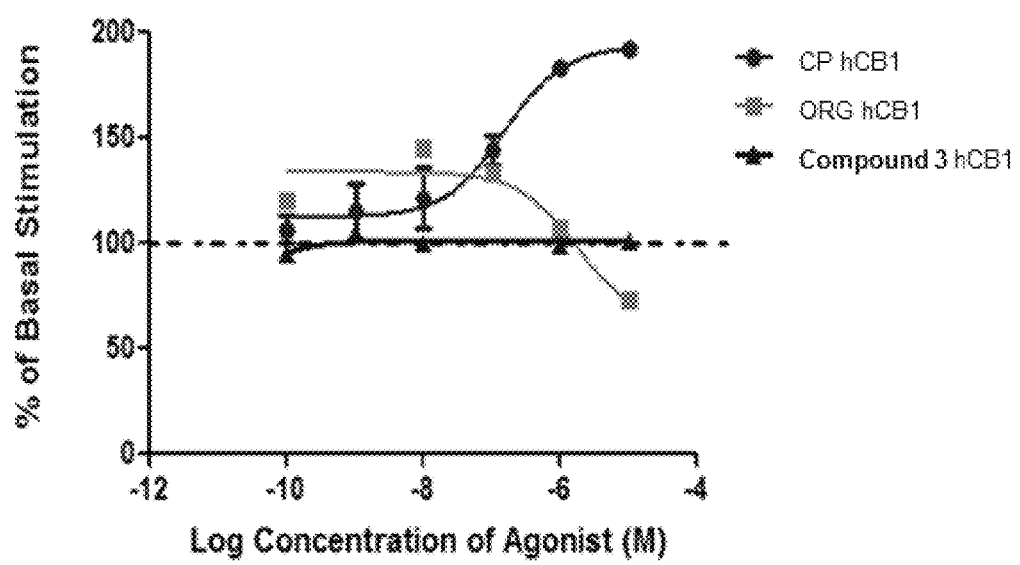
FIG. 9 shows GTPγS stimulation levels in hCB$_1$/HEK cells upon treatment with a compound of the invention.

FIG. 9 shows GTPγS stimulation levels in $hCB_1$/HEK cells upon treatment with a compound of the invention. Compound 3 causes no effect on GTP-gamma-S binding at the human $CB_1$ receptor. CP55940 (CP), a $CB_1$ agonist, causes a rise in GTP-gamma-S binding, while the $CB_1$ inverse agonist, ORG27569 (ORG) causes a decrease (including below basal).

Figure 10:
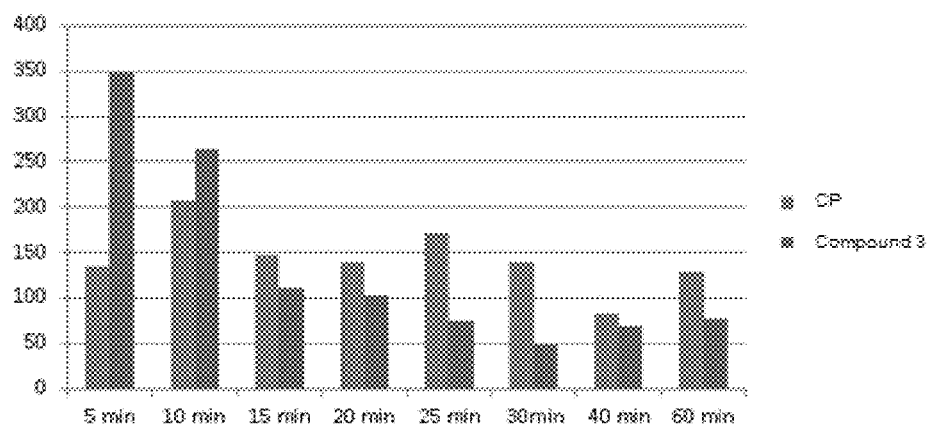
FIG. 10 shows pERK production in cells upon treatment with a compound of the invention.

FIG. 10 shows pERK production in cells upon treatment with a compound of the invention. Compound 3 causes a robust effect, particularly at early time points, compared to CP (CP55,940).

Compound 1 and Compound 2—

These analogs of OR27569 were designed to form a new hydrogen bond with the transmembrane helix 6 residue, D6.58(366). To form this new interaction, a hydroxyl group was added to the carbon adjacent to the phenyl ring of the ORG27569. Attaching a hydroxyl group to this carbon makes the carbon chiral, meaning that the hydroxyl can be added in two different ways (forming an S or an R enantiomer). The S enantiomer is compound 1 and the R enantiomer is compound 2 (see FIG. 1). These compounds were designed to test predictions made by our computational models. The results of our molecular modeling calculations suggest that each compound can adopt an energetically accessible conformation that enables the compound to form a hydrogen bond with D6.58(366). However, this new interaction changes how each compound binds to the $CB_1$/CP55,940 complex, resulting from the receptor's topography at the compounds' binding site, as well as the geometry about each enantiomers hydroxyl group.

Specifically, the models suggest that the hydroxyl group of compound 1 causes the compound to shift in its binding site, as compared to ORG27569. This binding site difference is due to an energetic impetus to optimize the geometry of the hydrogen bond between D6.58(366) and the compound 1's hydroxyl group. As a result, compound 1 is unable to form a hydrogen bond with K3.28(192), and forms less productive interactions with the $CB_1$/CP55,940 complex (as compared to ORG27569). The predicted weaker interactions between compound 1 and the $CB_1$/CP55,940 complex is consistent with our experimental results. First, compound 1 does not improve CP55,940's $B_{max}$ as well as ORG27569 (see FIG. 3). Second, compound 1 does not antagonize CP55,940's [$^{35}$S]GTPλS signaling as well as ORG27569 (see FIG. 3). Finally, compound 1 (when applied alone) does not act as an inverse agonist of [$^{35}$S]GTPλS signaling (see FIG. 4); this is consistent with prior work that suggests that an interaction between the compound's piperidine ring and K3.28(192) may be necessary for the compound to act as an inverse agonist (Shore, supra).

Likewise, the models also suggest that the hydroxyl group of compound 2 causes the compound to shift in its binding site, as compared to ORG27569. This binding site difference is due to an energetic impetus to optimize the geometry of the hydrogen bond between D6.58(366) and the compound 2's hydroxyl group. Also like compound 1, this binding site difference prevents compound 2 from forming a hydrogen bond with K3.28(192). However, in contrast with compound 1, this binding site change improves compound 2's interactions with the $CB_1$/CP55,940 complex; specifically, compound 2 forms improved hydrophobic interactions, as well as forms a new hydrogen bond between its piperidine nitrogen and a hydroxyl group of CP55,940. Altogether, our models predict that compound 2 has better interactions with the $CB_1$/CP55,940 complex than ORG27569. The predicted improved interactions between compound 2 and the $CB_1$/CP55,940 complex is consistent with our experimental results. First, compound 2 improves CP55,940's $B_{max}$ better than as ORG27569 (see FIG. 3). Second, compound 2 antagonizes CP55,940's [$^{35}$S]GTPλS signaling as well as ORG27569 (see FIG. 3). Finally, compound 2 (when applied alone) does not act as an inverse agonist of [$^{35}$S]GTPλS signaling (see FIG. 5); this is consistent with prior work that suggests that an interaction between the compound's piperidine ring and K3.28(192) may be necessary for the compound to act as an inverse agonist (Shore, supra). Interestingly, in mouse membranes, compound 2 may act as a weak agonist of G protein-mediated signaling, suggesting a unique pharmacological profile as compared to ORG27569 (see FIG. 5).

Compound 3—

This analog of ORG27569 was designed to answer two hypotheses informed by our computational models: 1) whether ORG27569 could tolerate the addition of steric bulk in a region that the model suggests packs against TMH6-7; 2) if the addition of steric bulk on the compound's phenyl ring would impact the ability of the compound to act as an allosteric modulator of $CB_1$. Specifically, to create compound 3, a cyclopropyl group was attached to the compound's phenyl ring (see FIG. 1). The models suggests that even if compound 3 were able to enter the receptor, it may not be able to act as an allosteric modulator, because the newly added cyclopropyl group would have steric clashes with residues on TMH6/7. These results are consistent with our experimental results that suggests that compound 3 does not improve CP55,940's $B_{max}$ (and may actually reduce it); in addition, compound 3 was not observed to antagonize CP55,940's [$^{35}$S]GTPλS signaling (see FIG. 3). In addition, compound 3 did not have any significant effect on [$^{35}$S]GTPλS signaling when applied alone (see FIG. 9). Altogether, these results suggest that compound 3 does not act as an allosteric modulator of $CB_1$.

However, our molecular dynamics simulations of ORG27569 and our inactive $CB_1$ receptor model, suggest that ORG27569 induces a receptor conformational change by inserting its indole ring between TMH6/7 (see FIG. 2A). This conformational change is consistent with activation of the ERK signaling pathway. In addition, this insertion of ORG27569's indole ring does not require that the compound leave the lipid bilayer and fully bind inside the receptor's transmembrane core. Based on these results, our models suggests that compound 3 may be able to insert its indole ring between TMH6-7, generating an ERK signal; however, because of the steric bulk introduced by its cyclopropyl ring, it may not be able to bind inside of $CB_1$ (preventing its ability to impact G protein-mediated signaling). These computational results are consistent with our experimental results. As just described, compound 3 does not act as an allosteric modulator of $CB_1$ (see FIG. 3), nor does it impact G protein-mediated signaling when applied alone (see FIG. 9). However, compound 3 does generate an ERK signal (see FIG. 10). This suggests that it is possible to design $CB_1$ ERK-pathway biased ligands by creating compounds that insert between TMH6/7, but are unable to fully insert into the receptor's transmembrane core.

Compound 4—

This analog of OR27569 was designed to form a new aromatic interaction with the transmembrane helix 3 residue, F3.25(189). To form this new interaction, the ethyl group attached to the indole ring of ORG27569 was replaced with a benzyl group (see FIG. 1). The results of our molecular modeling calculations suggest that compound 4 can adopt an energetically accessible conformation that enables the compound to form an aromatic stack with F3.25(189). However, this new interaction changes how the compound binds to the $CB_1$/CP55,940 complex, resulting from the receptor's topography at the compounds' binding site, as well as the geometry about the benzyl group of the compound. As a result, compound 4 is unable to form a hydrogen bond with K3.28(192). However, due to the new aromatic interaction with F3.25(189), as well as improved hydrophobic interactions in general, compound 4 forms more productive interactions with the $CB_1$/CP55,940 complex (as compared to ORG27569). Interestingly, compound 4 did not affect CP55,940's $B_{max}$ (see FIG. 3). However, compound 4 antagonized CP55,940's [$^{35}$S]GTPλS signaling as well as ORG27569 (see FIG. 3). Finally, compound 4 (when applied alone) does not act as an inverse agonist of [$^{35}$S]GTPλS signaling (see FIG. 7); this is consistent with prior work that suggests that an interaction between the compound's piperidine ring and K3.28(192) may be necessary for the compound to act as an inverse agonist (Shore, supra). In addition, compound 4 (when applied alone) may act as a weak inverse agonist of ERK signaling, suggesting a unique pharmacological profile as compared to ORG27569 (see FIG. 8).

Although the foregoing invention has been described in some detail by way of illustration and example for purposes of clarity of understanding, one of skill in the art will appreciate that certain changes and modifications can be practiced within the scope of the appended claims. In addition, each reference provided herein is incorporated by reference in its entirety to the same extent as if each reference was individually incorporated by reference.

What is claimed is:

1. A compound having the Formula I:

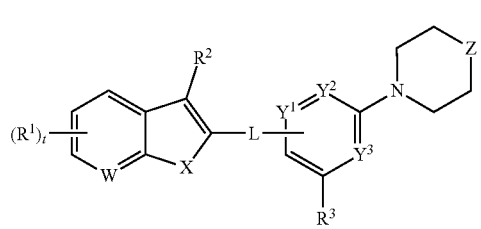

(I)

or a pharmaceutically acceptable salt thereof;
wherein
R$^1$ is selected from the group consisting of halo, cyano, nitro, and acetyl;
R$^2$ is C$_{1-12}$ alkyl,
R$^3$ is selected from the group consisting of H, C$_3$-C$_{12}$ alkyl, C$_3$-C$_8$ cycloalkyl, 4- to 8-membered heterocyclyl, C$_6$-C$_{10}$ aryl, and 5- to 10-membered heteroaryl;
W is selected from the group consisting of N and CR$^{1a}$, wherein R$^{1a}$ is selected from the group consisting of H and R';
X is selected from the group consisting of O, C=O, and NR$^4$, wherein R$^4$ is selected from the group consisting of H and C$_{1-6}$ alkyl;
Y$^1$, Y$^2$, and Y$^3$ are independently selected from the group consisting of N and CH;
Z is selected from the group consisting of O, CH$_2$, and NR$^4$, wherein R$^4$ is selected from the group consisting of H and C$_{1-6}$ alkyl;
subscript t is 0 when W is CR$^{1a}$ and R$^{1a}$ is R$^1$;
subscript t is 1 when W is N or when W is CR$^{1a}$ and R$^{1a}$ is H; and
L is selected from the group consisting of

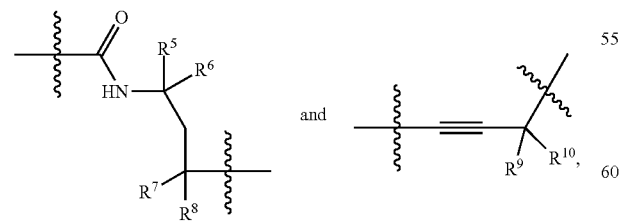

wherein
R$^5$ and R$^6$ are H,
R$^7$ is H and R$^8$ is OH, or
R$^7$ is OH and R$^8$ is H, or R$^5$ and R$^7$ are absent and R$^6$ and R$^8$ are taken together to form a 5- to 6-membered unsaturated carbocyclic or heterocyclic group, and
R$^9$ and R$^{10}$ are independently selected from the group consisting of H and OH, provided that at least of R$^9$ and R$^{10}$ is H.

2. The compound of claim 1, which is selected from the group consisting of:

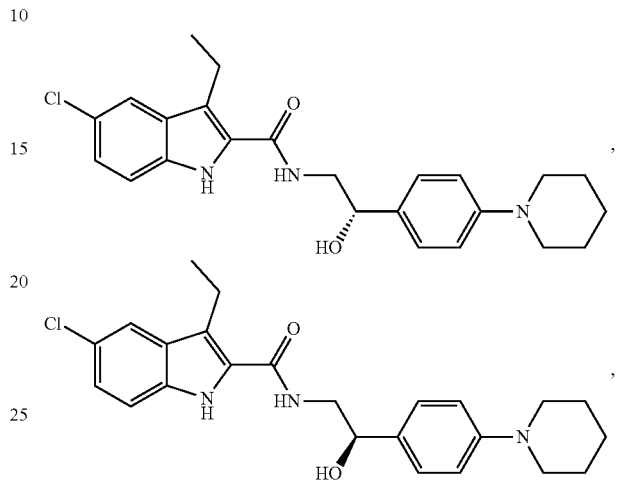

and pharmaceutically acceptable salts thereof.

3. The compound of claim 1, according to the formula

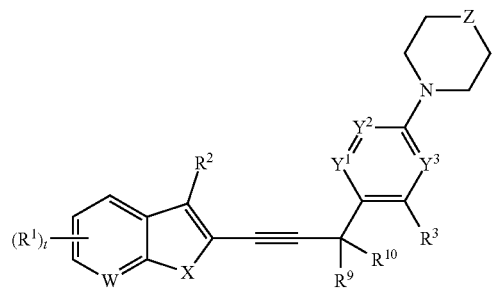

or a pharmaceutically acceptable salt thereof.

4. The compound of claim 3, according to the formula

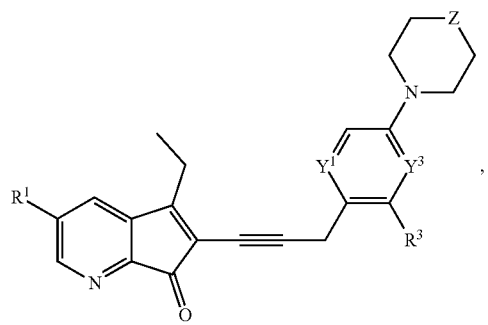

or a pharmaceutically acceptable salt thereof, wherein
R$^1$ is selected from the group consisting of Cl and F; and
R$^3$ is selected from the group consisting of H, C$_3$-C$_8$ cycloalkyl, and 4- to 8-membered heterocyclyl.

5. The compound of claim 4, which is selected from the group consisting of:

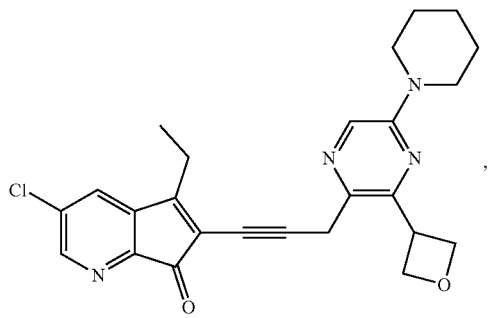

and pharmaceutically acceptable salts thereof.

6. The compound of claim 1, according to the formula

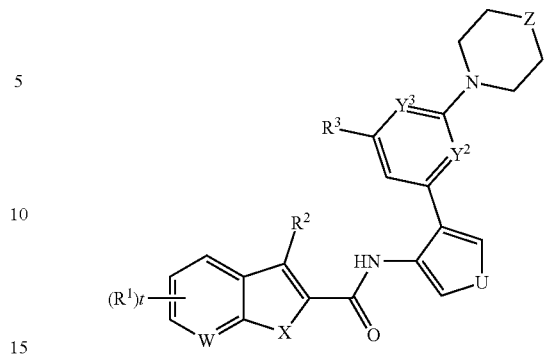

or a pharmaceutically acceptable salt thereof, wherein U is selected from the group consisting of S and O.

7. The compound of claim 6, which is selected from the group consisting of:

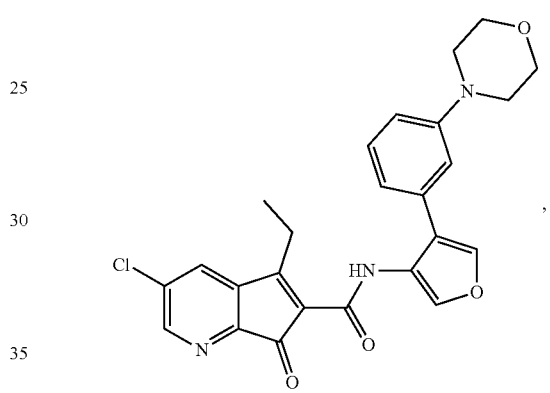

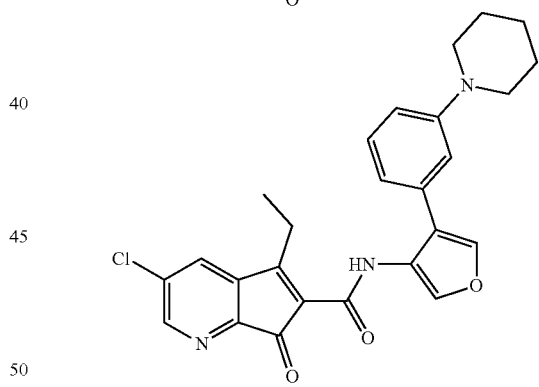

and
pharmaceutically acceptable salts thereof.

8. A pharmaceutical composition comprising a compound of claim 1 and one or more pharmaceutically acceptable excipients.

9. A kit comprising a composition of claim 8 and instructions for use.

10. A method of treating a condition or disorder mediated in part by $CB_1$ receptor activity in a patient having the condition or disorder, the method comprising administering to the patient an effective amount of a compound of claim 1.

11. The method of claim 10, wherein the condition is selected from the group consisting of glaucoma, pain, nausea, neurodegeneration, and appetite loss.

* * * * *